(12) United States Patent
Tryggvason et al.

(10) Patent No.: US 11,655,451 B2
(45) Date of Patent: May 23, 2023

(54) METHODS FOR CULTURING HUMAN KERATINOCYTES

(71) Applicants: National University of Singapore, Singapore (SG); Singapore Health Services Pte Ltd, Singapore (SG)

(72) Inventors: Karl Tryggvason, Singapore (SG); Monica Suryana Tjin, Singapore (SG); Alvin Wen Choong Chua, Singapore (SG)

(73) Assignees: NATIONAL UNIVERSITY OF SINGAPORE, Singapore (SG); SINGAPORE HEALTH SERVICES PTE LTD, Singapore (SG)

( * ) Notice: Subject to any disclaimer, the term of this patent is extended or adjusted under 35 U.S.C. 154(b) by 362 days.

(21) Appl. No.: 16/610,971

(22) PCT Filed: May 4, 2018

(86) PCT No.: PCT/SG2018/050220
§ 371 (c)(1),
(2) Date: Nov. 5, 2019

(87) PCT Pub. No.: WO2018/203834
PCT Pub. Date: Nov. 8, 2018

(65) Prior Publication Data
US 2020/0071666 A1 Mar. 5, 2020

Related U.S. Application Data

(60) Provisional application No. 62/501,992, filed on May 5, 2017.

(51) Int. Cl.
*C12N 5/071* (2010.01)
*A61K 35/36* (2015.01)
*C12N 5/00* (2006.01)

(52) U.S. Cl.
CPC ............ *C12N 5/0629* (2013.01); *A61K 35/36* (2013.01); *C12N 5/0068* (2013.01); *C12N 5/0698* (2013.01); *C12N 2500/02* (2013.01); *C12N 2500/90* (2013.01); *C12N 2500/98* (2013.01); *C12N 2533/52* (2013.01)

(58) Field of Classification Search
None
See application file for complete search history.

(56) References Cited

U.S. PATENT DOCUMENTS

| | | | | |
|---|---|---|---|---|
| 2012/0302512 A1* | 11/2012 | Tryggvason | ............ | C07K 14/78 530/395 |
| 2013/0280750 A1 | 10/2013 | Tryggvason et al. | | |
| 2016/0102289 A1 | 4/2016 | Yu et al. | | |
| 2016/0348070 A1 | 12/2016 | Kirkeby et al. | | |
| 2017/0002089 A1* | 1/2017 | Liu | ................... | G01N 33/6854 |

FOREIGN PATENT DOCUMENTS

| | | | |
|---|---|---|---|
| JP | 200254824 | A | 12/2002 |
| JP | 2009226207 | A | 9/2009 |
| JP | 2012120531 | A | 6/2012 |
| JP | 2013521795 | A | 6/2013 |
| JP | 2013545489 | A | 12/2013 |
| WO | 2005/087286 | A1 | 9/2005 |
| WO | 2015046315 | A1 | 4/2015 |
| WO | 2016061071 | A1 | 4/2016 |
| WO | 2016/131959 | A1 | 8/2016 |
| WO | WO 2016/162747 | A2 | 10/2016 |
| WO | 2017/002888 | A1 | 1/2017 |

OTHER PUBLICATIONS

Alitalo et al., The Journal of Cell Biology, vol. 94, Sep. 1982, pp. 497-505 (Year: 1982).*
Boyce et al., Journal of Tissue Culture Methods, vol. 9, No. 2, 1985, Procedure No. 41406 pp. 83-93 (Year: 1985).*
Coolen et al., Cell Transplantation, vol. 16, pp. 649-661, 2007 (Year: 2007).*
Pennybaker et al., Xeno-Free, CellCultureDish.com, retrieved from the internet Mar. 11, 2022:https://cellculturedish.com/xeno-free-what-is-it/ (Year: 2022).*
Doi et al., The Journal of Biological Chemistry, vol. 277, No. 15, Apr. 12, 2002, pp. 12741-12748 (Year: 2002).*
Ng et al., Acta Derm Venereol 2011; 91: 387-391 (Year: 2011).*
Paulsson et al., Cytotechnology 9: 99-106, 1992 (Year: 1992).*
Richards Tissue Engineering: Part c, vol. 14, No. 3, 2008, pp. 1-12 (Year: 2008).*
Ryu J. Radiat. Res., 50, 545-552 (2009) (Year: 2009).*
Sun Wound Repairand Regeneration, vol. 12, No. 6, 2004, pp. 626-634 (Year: 2004).*
Iorio et al: "Laminins: Roles and Utility in Wound Repair", Advances in Wound Care, vol. 4, No. 4, Apr. 1, 2015 (Apr. 1, 2015), pp. 250-263, XP055487848, ISSN: 2162-1918, DOI: 10.1089/wound.2014.0533.
Pouliot et al: "Laminin 10/11: an alternative adhesive ligand for epidermal keratinocytes with a functional role in promoting proliferation and migration", Experimental Dermatology, vol. 11, No. 5, Oct. 1, 2002 (Oct. 1, 2002), pp. 387-397, XP055487942, Copenhagen; DK ISSN: 0906-6705, DOI: 10.1034/j.1600-0625.2002.110501.x.
Steffens et al: "Development of a biomaterial associated with mesenchymal stem cells and keratinocytes for use as a skin substitute", Regenerative Medicine, vol. 10, No. 8, Nov. 1, 2015 (Nov. 1, 2015), pp. 975-987, XP055488021, GB ISSN: 1746-0751, DOI: 10.2217/rme.15.58.

(Continued)

*Primary Examiner* — Evelyn Y Pyla
(74) *Attorney, Agent, or Firm* — Lippes Mathias LLP

(57) ABSTRACT

The present disclosure relates to methods for culturing human epidermal keratinocytes. When keratinocytes are cultured on plates coated with a laminin containing an alpha-4 chain or an alpha-5 chain, in a xeno-free, chemically defined cell culture medium, they expand efficiently in vitro. Useful cell culture kits for culturing keratinocytes are also described herein, as are methods of using such cells for treatment of burns or chronic wounds.

12 Claims, 13 Drawing Sheets

(56) References Cited

OTHER PUBLICATIONS

Wegner et al: "Laminin [alpha]5 in the keratinocyte basement membrane is required for epidermal-dermal intercommunication", Matrix Biology, vol. 56, May 24, 2016 (May 24, 2016), pp. 24-41, XP029830789, ISSN: 0945-053X, DOI: 10.1016/J.MATBI0.2016.05.001.
International Search Report dated Jul. 13, 2018 from PCT/SG2018/050220.
Zenebech Wondimu, et al, "Characterization of commercial laminin preparations from human placenta in comparison to recombinant laminins 2" Matrix Biology 25 (2006) pp. 1-5.
Maia M. Alexaline, et al, "Bioengineering in a Human Plasma-Based Epidermal Substitute with Efficient Grafting Capacity and High Content in Clongoneic Cells" Stem Cells Translational Medicine, 2015 pp. 1-12.

* cited by examiner

FIG. 1A (No coating)
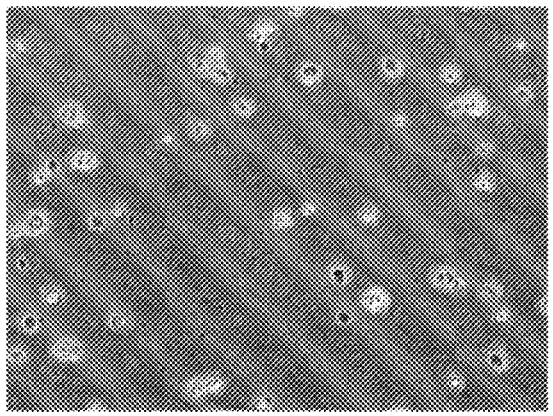
FIG. 1B (3T3)
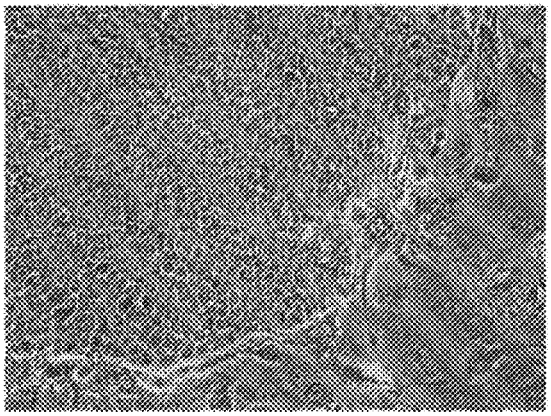
FIG. 1C (LN-111)
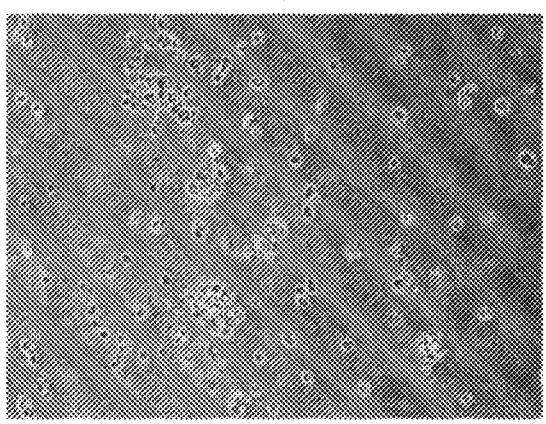
FIG. 1D (LN-332)
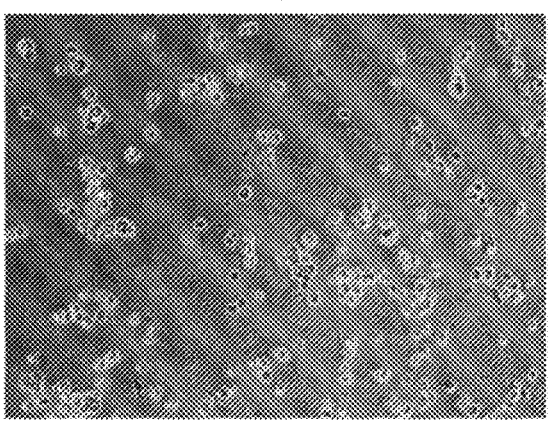
FIG. 1E (LN-411)
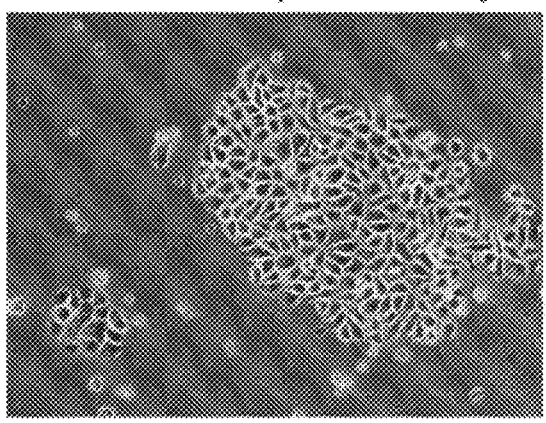
FIG. 1F (LN-421)
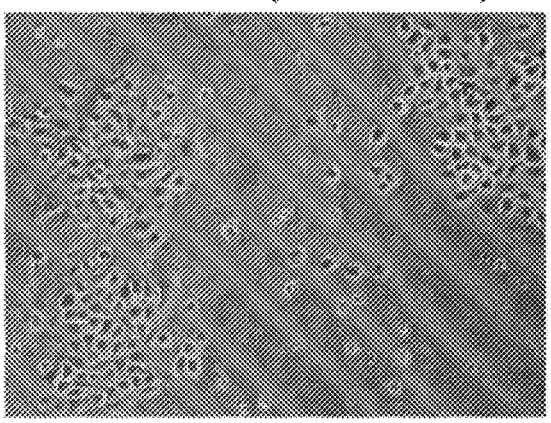

FIG. 1G (LN-511)
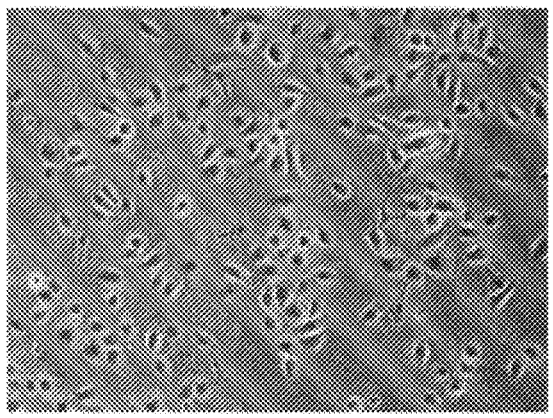
FIG. 1H (LN-521)
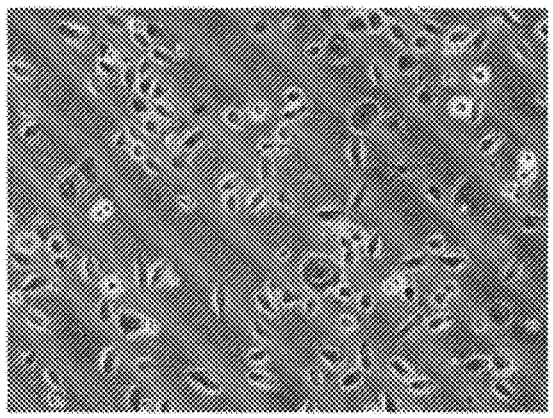
FIG. 1I (LN-421/511, 10:1)
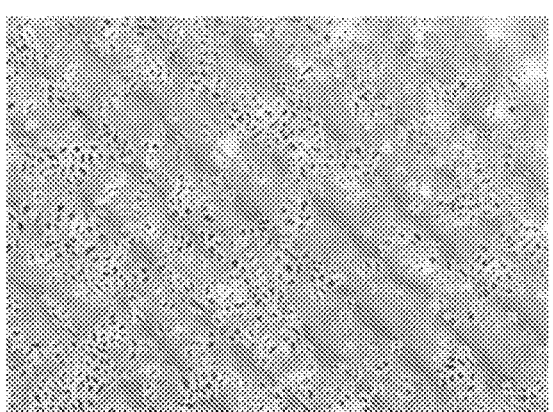
FIG. 1J (LN-421/511, 1:10)
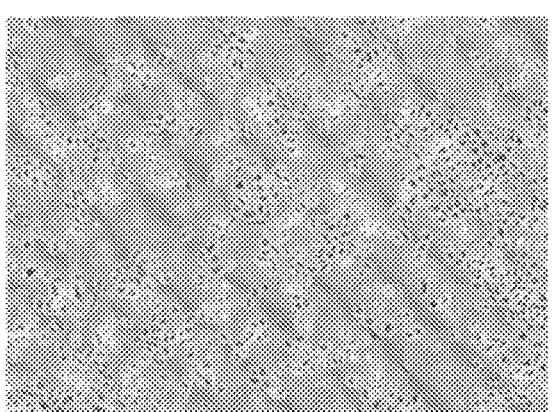

LN-511
KRT5/DAPI

LN-511
KRT14/DAPI

LN-511
KRT15/DAPI

LN-511
p63/DAPI

LN-511
IVL/DAPI

LN-511
KRT10/DAPI

LN-511
KRT1/DAPI

LN-421
KRT5/DAPI

LN-421
KRT14/DAPI

LN-421
KRT15/DAPI

LN-421
p63/DAPI

LN-421
IVL/DAPI

LN-421
KRT10/DAPI

LN-421
KRT1/DAPI

3T3

LN-511

LN-421

FIG. 8A (3T3)
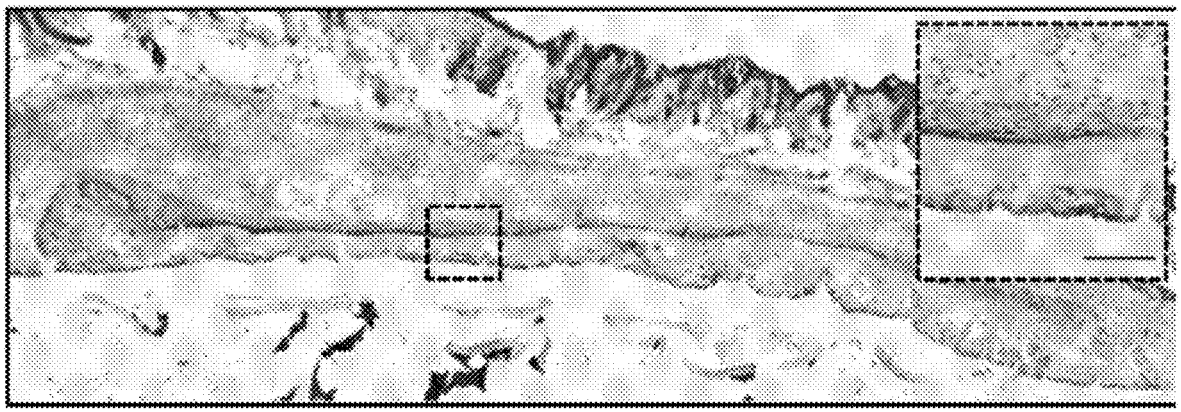
FIG. 8B (LN-421)
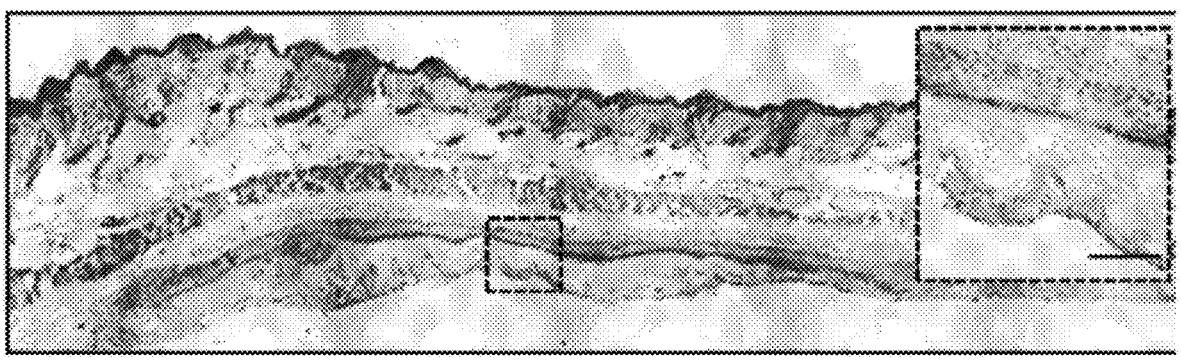
FIG. 8C (LN-511)
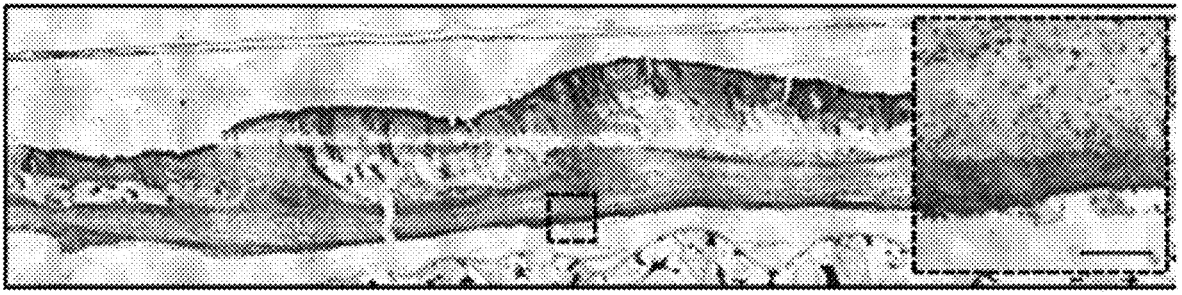

METHODS FOR CULTURING HUMAN KERATINOCYTES

CROSS-REFERENCE TO RELATED APPLICATIONS

This application claims priority to U.S. Provisional Patent Application Ser. No. 62/501,992, filed May 5, 2017, which is hereby fully incorporated by reference.

BACKGROUND

The present disclosure relates to methods for culturing human epidermal keratinocytes. These keratinocytes can then be used in therapies such as for treating severe burns minor burns, and chronic wounds. Other potential therapeutic applications of these cultured cells can be for the treatment of any epithelial injuries or conditions in the human body (such as in the eye, bladder, oral cavity, intestine, etc.), including cases in which only the epithelium is compromised, or in which sub-epithelial components are also damaged. Also disclosed are kits for practicing the methods. Very generally, the keratinocytes are cultured on a substrate of Laminin-411, Laminin-421, Laminin-511, and/or Laminin-521, and exposed to serum-free medium to support keratinocytes survival in vitro without the aid of feeder cells.

Burn injuries remain a huge clinical problem as autologous donor sites become insufficient to provide primary cover for wound closure when the total body surface area (TBSA) exceeds 40%. One technology developed to overcome this problem is the use of cultured epithelial autografts (CEA). This method involves the isolation and serial expansion of skin epidermal keratinocytes from a small skin biopsy to obtain large amount of cultured epithelium for definitive wound coverage within a 3 to 4 week period. Since the report of permanent coverage of large burn wounds with autologous cultured human epithelium, this technology has been used successfully worldwide to treat severe burns, in what is frequently a life-saving procedure.

This current gold standard protocol for culturing human epidermal keratinocytes for severe burn treatment requires the use of some animal-derived products (e.g., bovine serum and murine 3T3 fibroblasts as feeder cells). Such products do not meet clinical quality criteria which are common in today's cell therapy environment. The presence of murine cells carries the risk of exposing human cell culture to animal pathogens and immunogenic agents. Moreover, fetal bovine serum (FBS) used in the culture media is undefined and has batch-to-batch variation.

To overcome this problem, serum-free and xeno-free cell culture media have been developed for keratinocyte cultures. However, these systems remain non-optimal and none are used in clinical applications for severe wound defects. It has been demonstrated that culturing keratinocytes using serum-free keratinocyte growth media without the use of irradiated 3T3 feeder cells could not preserve the proliferative capacity of keratinocytes compared to those supported by feeder cells.

It would be desirable to develop methods for supporting keratinocyte survival and expansion in vitro without the aid of 3T3 feeder cells and animal-derived serum.

BRIEF DESCRIPTION

The present disclosure provides methods for culturing human epidermal keratinocytes. These keratinocytes can then be used in therapies such as treating and managing less severe burns and chronic wounds. More particularly, this disclosure also describes a novel system for culturing human epidermal keratinocytes in a completely xeno-free and fully human method. By using pure laminin matrices (for example, LN-511 and/or LN-421) and chemically defined, serum-free medium, this method supports keratinocyte survival in vitro without the aid of feeder cells and xenobiotic components, with as many as 30 population doublings in adult patient cells. In further aspects, the present disclosure provides a kit for culturing keratinocytes.

FACS analysis and immunofluorescence staining confirm that cells grown in this system express keratinocytes basal markers KRT5, KRT14, KRT15, ITGA6, and ITGB1. Differentiation markers KRT1 and KRT10 are expressed normally at the later passage. Real-time Quantitative PCR analyses (qPCR) carried out at different time points show the keratinocyte basal and differentiation profile over increasing passages.

In some aspects, the disclosure describes the plating of keratinocytes on a substrate of Laminin-411 (LN-411), Laminin-421 (LN-421), Laminin-511 (LN-511), or Laminin-521 (LN-521), and culturing the cells using a cell culture medium. In other words, the laminin used in the substrate contains an alpha-4 or alpha-5 chain. In particular embodiments, the cell culture medium is xeno-free. The cells may be passaged with Trypsin EDTA prior to plating.

In particular aspects the cell culture medium is a basal medium. According to some embodiments, the basal medium includes insulin and chemically defined growth supplement. Other ingredients can include human epidermal growth factor (hEGF); hydrocortisone; and antibiotics and/or antifungals such as gentamicin or amphotericin B. The insulin may be recombinant human insulin. In additional embodiments, the basal medium further includes epinephrine and transferrin.

In some embodiments, freshly isolated keratinocytes may be plated on the substrate at a density of about $1 \times 10^5/cm^2$. In specific aspects, keratinocytes are cultured in an atmosphere containing from about 5% $CO_2$ to about 15% $CO_2$. The keratinocytes may be cultured at a temperature from about 30 degrees Celsius to about 40 degrees Celsius.

In other embodiments, the keratinocytes may be trypsinized at a temperature from about 30 degrees Celsius to about 40 degrees Celsius. In particular embodiments, keratinocytes are trypsinized for a period of about 4 minutes to about 12 minutes. In more specific embodiments, keratinocytes are trypsinized for a period of about 6 minutes to about 10 minutes. In further particular embodiments, keratinocytes are passaged upon reaching a density of about $1 \times 10^4$ cells/cm$^2$.

Also disclosed is a system for maintaining keratinocytes, comprising a substrate containing Laminin-411, Laminin-421, Laminin-511, and/or Laminin-521 and a cell culture medium. In particular aspects, the cell culture medium is xeno-free. In other aspects, the cell culture medium does not contain animal serum.

The present disclosure also describes a kit for culturing keratinocytes in vitro. The kit includes: a cell culture plate with a coating of Laminin-411, Laminin-421, Laminin-511, and/or Laminin-521; and a cell culture medium, wherein the cell culture medium is serum-free.

Also disclosed herein are methods for treating a burn wound of a patient. Keratinocyte cells taken from a donor site of the patient are plated on a substrate coated with Laminin-411, Laminin-421, Laminin-511, and/or Laminin- 521. The keratinocyte cells are expanded on the substrate. The keratinocyte cells from the substrate are then used to cover the burn wound.

Also disclosed herein are methods for treating a chronic wound of a patient. Keratinocyte cells taken from a donor site of the patient are plated on a substrate coated with Laminin-411, Laminin-421, Laminin-511, and/or Laminin-521. The keratinocyte cells are expanded on the substrate. The keratinocyte cells from the substrate are then used to cover the wound.

Also disclosed herein are methods for treating any injuries or conditions in the human body, including cases in which only the epithelium is compromised, and/or in which an epithelium defect is a component of the injury. Keratinocyte cells taken from a donor site of the patient are plated on a substrate coated with Laminin-411, Laminin-421, Laminin-511, and/or Laminin-521. The keratinocyte cells are expanded on the substrate. The keratinocyte cells from the substrate are then used to cover the epithelium defect.

Also disclosed herein is the use of keratinocytes for the treatment of burn wounds, chronic wounds, and other epithelium defects. Desirably, the keratinocytes were plated and expanded on a substrate coated with Laminin-411, Laminin-421, Laminin-511, and/or Laminin-521.

These and other non-limiting characteristics of the disclosure are more particularly disclosed below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

FIGS. 1A-1J are a set of images of freshly isolated human epidermal keratinocytes cultured on various laminin matrices and compared to a negative control substrate containing no laminin and a positive control substrate where the keratinocytes were co-cultured with 3T3 fibroblasts. Freshly isolated human epidermal keratinocytes were cultured on LN-411, LN-421, LN-511, LN-521, LN-111, LN-332, and tissue culture dish without coating (negative control) in KGM-CD medium. Images were taken at day 7. Scale bar=100 micrometers (μm). FIG. 1A is the negative control (no coating). FIG. 1B is the positive control (3T3). FIG. 1C is the substrate with only LN-111. FIG. 1D is the substrate with only LN-332. FIG. 1E is the substrate with only LN-411. FIG. 1F is the substrate with only LN-421. FIG. 1G is the substrate with only LN-511. FIG. 1H is the substrate with only LN-521. FIG. 1I is a substrate containing LN-421 and LN-521 in a 10:1 ratio (w/w/). FIG. 1J is a substrate containing LN-421 and LN-521 in a 1:10 ratio (w/w/).

FIG. 2A is for 3T3. FIG. 2B is for LN-511. FIG. 2C is for LN-421.

FIG. 2D is a graph showing the number of cumulative population doublings for keratinocytes cultured on LN-411 (circles), LN-421 (diamonds), LN-511 (triangles), or LN-521 (squares). The y-axis runs from 0 to 20 in increments of 5, and the x-axis runs from 0 days to 60 days in increments of 10. The LN-511 and LN-421 lines have more population doublings than LN-411 or LN-521.

FIG. 3A is for KRT5. FIG. 3B is for KRT14. FIG. 3C is for KRT1. FIG. 3D is for KRT10.

FIG. 4A is LN-511, for KRT5. FIG. 4N is LN-421, for KRT1.

Freshly isolated human epidermal keratinocytes (passage 0) were plated on either LN-511, LN-421, or co-cultured with 3T3-fibroblasts feeder cells (Rheinwald & Green's method). After reaching confluency, cells were collected and subjected for FACS analysis for basal/progenitor markers (KRT5, KRT14, ITGA6, ITGB1, and KRT15) and differentiation markers (KRT1, KRT10).

FIG. 7A is the cross-section with keratinocytes previously co-cultured with 3T3. FIG. 7B is the cross-section with keratinocytes previously grown on LN-511. FIG. 7C is the cross-section with keratinocytes previously grown on LN-421

FIGS. 8A-8C are in vivo transplantation of human keratinocytes cultured on LN-511 or LN-421 in comparison with human keratinocytes grown on 3T3 co-culture system. Tissue was harvested after 8 days of grafting. Frozen sections were stained with H&E staining. FIG. 8A is the H&E staining of in vivo graft obtained from human keratinocytes previously co-cultured with 3T3. FIG. 8B is the H&E staining of in vivo graft obtained from human keratinocytes previously cultured on LN-421. FIG. 8C is the H&E staining of in vivo graft obtained from human keratinocytes previously cultured on LN-511.

DETAILED DESCRIPTION

Figure 2A:
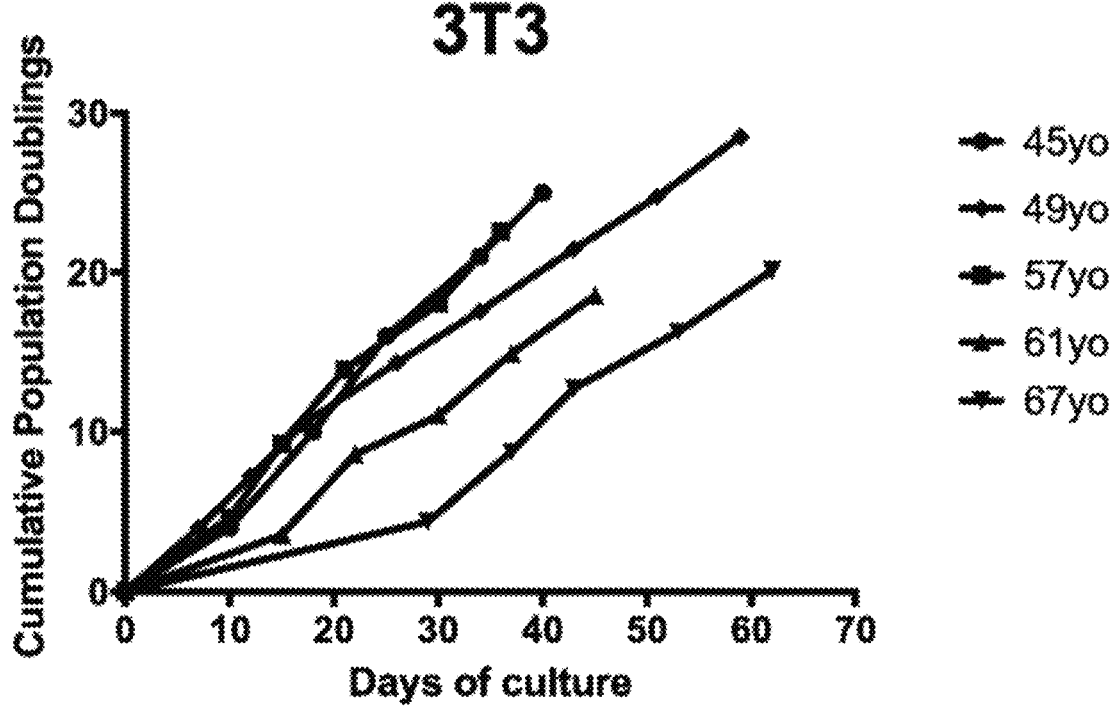
FIGS. 2A-2D are a set of graphs showing the growth rate of keratinocytes cultured on LN-511 and LN-421, compared to the conventional Rheinwald & Green's method: co-cultured with 3T3 murine fibroblasts (labeled as 3T3), as described in *Cell*, 6, 331-343 (1975). Keratinocytes obtained from persons of different ages were cultured. Upon confluency, cells were harvested, counted, and passaged until they reached senescence. Population doubling was calculated as PD=3.32× log (number of cell harvested/number of cells seeded). For FIGS. 2A-2C, the y-axis runs from 0 to 30 in increments of 10, and the x-axis runs from 0 days to 70 days in increments of 10.

A more complete understanding of the compositions and methods disclosed herein can be obtained by reference to the accompanying drawings. These figures are merely schematic representations based on convenience and the ease of demonstrating the present disclosure, and are, therefore, not intended to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 to 10" is inclusive of the endpoints, 2 and 10, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

All publications, patents, and patent applications discussed herein are hereby incorporated by reference in their entireties.

Several well-known references that may be relevant to the present disclosure include: *Molecular Cloning: A Laboratory Manual* (Sambrook, et al., 1989, Cold Spring Harbor Laboratory Press); *Gene Expression Technology* (Methods in Enzymology, Vol. 185, edited by D. Goeddel, 1991. Academic Press, San Diego, Calif.); "*Guide to Protein Purification*" in Methods in Enzymology (M. P. Deutshcer, ed., (1990) Academic Press, Inc.); *PCR Protocols: A Guide to Methods and Applications* (Innis, et al. 1990. Academic Press, San Diego, Calif.); *Culture of Animal Cells: A Manual of Basic Technique*, Second Ed. (R. I. Freshney. 1987. Liss, Inc. New York, N.Y.); *Gene Transfer and Expression Protocols*, pp. 109-128, ed. E. J. Murray, The Humana Press Inc., Clifton, N.J.); or the Ambion 1998 Catalog (Ambion, Austin, Tex.).

A keratinocyte is an epidermal cell that produces keratin. Keratinocytes are the predominant cells in the epidermis, the outermost layer of the skin, constituting 90% of the cells found there. Those keratinocytes found in the basal layer (stratum basale) of the skin are sometimes referred to as "basal cells" or "basal keratinocytes." The primary function of keratinocytes is the formation of a barrier against environmental damage, such as by pathogenic bacteria, fungi, parasites, and viruses, heat, UV radiation and water loss. Once pathogens start to invade the upper layers of the epidermis, keratinocytes can react by producing proinflammatory mediators, particularly chemokines.

One major reason for the loss of cellular phenotypes of primary cells cultured in vitro (such as keratinocytes) is a lack of normal cell-matrix interactions. In vivo, most organized cells such as human epidermal keratinocytes are tightly anchored to a special matrix known as the basement membrane (BM) or basal lamina. The BMs contain several specific components such as collagen IV, proteoglycans, and laminin proteins. The laminins are unique BM components, which exist in a large number of isoforms 16). Some isoforms are quite ubiquitous, while others are highly cell type specific. The laminin isoforms LN-511 and LN-521 are significant components of most embryonic and adult basement membranes and have important roles in development. These two isoforms, both of which are located in the BMs underlying the skin, have been shown to promote keratinocytes, stem cell adhesion, proliferation, migration, and possibly contribute to the maintenance of an undifferentiated phenotype in the stem cell population of the skin.

Laminins are a family of heterotrimeric glycoproteins that reside primarily in the basal lamina. They function via binding interactions with neighboring cell receptors on the one side and by binding to other laminin molecules or other matrix proteins such as collagens, nidogens or proteoglycans. The laminin molecules are also important signaling molecules that can strongly influence cellular behavior and function. Laminins are important in both maintaining cell/tissue phenotype, as well as in promoting cell growth and differentiation in tissue repair and development.

Laminins are large, multi-domain proteins, with a common structural organization. The laminin molecule integrates various matrix and cell interactive functions into one molecule.

A laminin protein molecule comprises one α-chain subunit, one β-chain subunit, and one γ-chain subunit, all joined together in a trimer through a coiled-coil domain. The twelve known laminin subunit chains can form at least 15 trimeric laminin types in native tissues. Within the trimeric laminin structures are identifiable domains that possess binding activity towards other laminin and basal lamina molecules, and membrane-bound receptors. For example, domains VI, IVb, and IVa form globular structures, and domains V, IIIb, and IIIa (which contain cysteine-rich EGF-like elements) form rod-like structures. Domains I and II of the three chains participate in the formation of a triple-stranded coiled-coil structure (the long arm).

There exist five different alpha chains, three beta chains and three gamma chains that in human tissues have been found in at least fifteen different combinations. These molecules are termed Laminin-1 to Laminin-15 based on their historical discovery, but an alternative nomenclature describes the isoforms based on their chain composition, e.g. Laminin-111 (previously termed Laminin-1) that contains alpha-1, beta-1 and gamma-1 chains. Four structurally defined family groups of laminins have been identified. The first group of five identified laminin molecules all share the β1 and γ1 chains, and vary by their α-chain composition (α1 to α5 chain). The second group of five identified laminin molecules, including Laminin-521, all share the β2 and γ1 chain, and again vary by their α-chain composition. The third group of identified laminin molecules has one identified member, Laminin-332, with a chain composition of α3β3γ2. The fourth group of identified laminin molecules has one identified member, Laminin-213, with the newly identified γ3 chain (α2β1γ3).

The methods of the present disclosure are generally related to culturing keratinocytes and encouraging their expansion. Particularly, the methods contemplate culturing keratinocytes on pure laminin matrices. Further, it is contemplated that the culturing system disclosed herein is completely xeno-free.

Adherent cells typically require two things to survive and reproduce: (1) a substrate or coating that provides a structural support for the cell; and (2) a cell culture medium to provide nutrition to the cell. The substrate or coating (1) is typically formed as a layer in a container, for example a petri dish or in a well of a multi-well plate. It is particularly contemplated that the substrate or coating on which the adherent cell is plated comprises a laminin.

Generally, the cell culture substrate of the present disclosure may contain any effective laminin, wherein the effectiveness is determined by whether keratinocytes can survive upon the substrate. It is specifically contemplated that the substrate contains only one particular laminin (i.e. one single laminin), though other ingredients may also be present in the substrate. In particular embodiments, the laminin is Laminin-511 (LN-511), Laminin-521 (LN-521), Laminin-411 (LN-411) or Laminin-421 (LN-421).

In other particular embodiments, the substrate may contain a combination of two particular laminins, i.e. any two of LN-511, LN-521, LN-411, and/or LN-421. In particular embodiments, the combination of two particular laminins is LN-511 and LN-421. The weight ratio of LN-511 to LN-421 in the substrate can range from 1:15 to 15:1, or from 1:10 to 10:1.

As used herein, the term "Laminin-521" refers to the protein formed by joining α5, β2 and γ1 chains together. The term should be construed as encompassing both recombinant Laminin-521 and heterotrimeric Laminin-521 from naturally occurring sources.

As used herein, the term "Laminin-511" refers to the protein formed by joining α5, β1 and γ1 chains together. The term should be construed as encompassing both recombinant Laminin-511 and heterotrimeric Laminin-511 from naturally occurring sources.

As used herein, the term "Laminin-421" refers to the protein formed by joining α4, β2 and γ1 chains together. The term should be construed as encompassing both recombinant Laminin-421 and heterotrimeric Laminin-421 from naturally occurring sources.

As used herein, the term "Laminin-411" refers to the protein formed by joining α4, β1 and γ1 chains together. The term should be construed as encompassing both recombinant Laminin-411 and heterotrimeric Laminin-411 from naturally occurring sources.

The laminin can be an intact protein or a protein fragment. The term "intact" refers to the protein being composed of all of the domains of the α-chain, β-chain, and γ-chain, with the three chains being joined together to form the heterotrimeric structure. The protein is not broken down into separate chains, fragments, or functional domains. The term "chain" refers to the entirety of the alpha, beta, or gamma chain of the laminin protein. The term "fragment" refers to any protein fragment which contains one, two, or three functional domains that possesses binding activity to another molecule or receptor. However, a chain should not be considered a fragment because each chain possesses more than three such domains. Similarly, an intact laminin protein should not be considered a fragment. Examples of functional domains include Domains I, II, III, IV, V, VI, and the G domain.

The cell culture substrate is used in combination with a cell culture medium. The cell culture medium of the present disclosure is particularly suitable for culturing keratinocytes in vitro. Typically, cell culture media include a large number and a large amount of various growth factors and cytokines to inhibit differentiation and improve proliferation.

Very generally, the cell culture medium of the present disclosure is a chemically defined, serum-free medium that includes a liquid phase. Table 1 below includes a list of various such ingredients that may be present in the cell culture medium of the present disclosure, and the minimum and maximum concentrations if the ingredient is present. The values are presented in scientific notation. For example, "4.1E-01" should be interpreted as $4.1 \times 10^{-01}$.

TABLE 1

| Ingredient | molar mass (g/mol) | Min. Conc. (mM) | Max. Conc. (mM) | Min. Conc. (ng/mL) | Max. Conc. (ng/mL) |
|---|---|---|---|---|---|
| INORGANIC SALTS | | | | | |
| Calcium chloride (Anhydrous) | 110.98 | 4.1E−01 | 1.6E+00 | 4.6E+04 | 1.8E+05 |
| HEPES | 238.3 | 5.9E+00 | 1.8E+01 | 1.4E+06 | 4.2E+06 |
| Lithium Chloride (LiCl) | 42.39 | 4.9E−01 | 1.5E+00 | 2.1E+04 | 6.2E+04 |

TABLE 1-continued

| Ingredient | molar mass (g/mol) | Min. Conc. (mM) | Max. Conc. (mM) | Min. Conc. (ng/mL) | Max. Conc. (ng/mL) |
| --- | --- | --- | --- | --- | --- |
| Magnesium chloride (Anhydrous) | 95.21 | 1.2E−01 | 3.6E−01 | 1.1E+04 | 3.4E+04 |
| Magnesium Sulfate ($MgSO_4$) | 120.37 | 1.6E−01 | 4.8E−01 | 1.9E+04 | 5.8E+04 |
| Potassium chloride (KCl) | 74.55 | 1.6E+00 | 4.9E+00 | 1.2E+05 | 3.6E+05 |
| Sodium bicarbonate ($NaHCO_3$) | 84.01 | 9.0E+00 | 4.4E+01 | 7.6E+05 | 3.7E+06 |
| Sodium chloride (NaCl) | 58.44 | 4.7E+01 | 1.4E+02 | 2.8E+06 | 8.3E+06 |
| Sodium phosphate, dibasic (Anhydrous) | 141.96 | 2.0E−01 | 5.9E−01 | 2.8E+04 | 8.3E+04 |
| Sodium phosphate, monobasic monohydrate ($NaH_2PO_4$—$H_2O$) | 137.99 | 1.8E−01 | 5.3E−01 | 2.4E+04 | 7.3E+04 |
| TRACE MINERALS | | | | | |
| Ferric Nitrate ($Fe(NO_3)_3$—$9H_2O$) | 404 | 4.9E−05 | 1.9E−04 | 2.0E+01 | 7.5E+01 |
| Ferrous sulfate heptahydrate ($FeSO_4$—$7H_2O$) | 278.01 | 5.9E−04 | 1.8E−03 | 1.6E+02 | 4.9E+02 |
| Copper(II) sulfate pentahydrate ($CuSO_4$—$5H_2O$) | 249.69 | 2.0E−06 | 8.0E−06 | 5.1E−01 | 2.0E+00 |
| Zinc sulfate heptahydrate ($ZnSO_4$—$7H_2O$) | 287.56 | 5.9E−04 | 1.8E−03 | 1.7E+02 | 5.1E+02 |
| Ammonium Metavanadate $NH_4VO_3$ | 116.98 | 5.5E−06 | 1.6E−05 | 6.4E−01 | 1.9E+00 |
| Manganese Sulfate monohydrate ($MnSO_4$—$H_2O$) | 169.02 | 9.9E−07 | 3.0E−06 | 1.7E−01 | 5.0E−01 |
| $NiSO_4$—$6H_2O$ | 262.85 | 4.9E−07 | 1.5E−06 | 1.3E−01 | 3.8E−01 |
| Selenium | 78.96 | 8.9E−05 | 2.7E−04 | 7.0E+00 | 2.1E+01 |
| Sodium Meta Silicate $Na_2SiO_3$—$9H_2O$ | 284.2 | 4.8E−04 | 1.4E−03 | 1.4E+02 | 4.1E+02 |
| $SnCl_2$ | 189.62 | 6.2E−07 | 1.9E−06 | 1.2E−01 | 3.5E−01 |
| Molybdic Acid, Ammonium salt | 1235.86 | 9.9E−07 | 3.0E−06 | 1.2E+00 | 3.7E+00 |
| $CdCl_2$ | 183.32 | 6.1E−06 | 1.8E−05 | 1.1E+00 | 3.4E+00 |
| $CrCl_3$ | 158.36 | 9.9E−07 | 3.0E−06 | 1.6E−01 | 4.7E−01 |
| $AgNO_3$ | 169.87 | 4.9E−07 | 1.5E−06 | 8.3E−02 | 2.5E−01 |
| $AlCl_3$—$6H_2O$ | 241.43 | 2.4E−06 | 7.3E−06 | 5.9E−01 | 1.8E+00 |
| Barium Acetate ($Ba(C_2H_3O_2)_2$) | 255.42 | 4.9E−06 | 1.5E−05 | 1.3E+00 | 3.8E+00 |
| $CoCl_2$—$6H_2O$ | 237.93 | 4.9E−06 | 1.5E−05 | 1.2E+00 | 3.5E+00 |
| $GeO_2$ | 104.64 | 2.5E−06 | 7.5E−06 | 2.6E−01 | 7.8E−01 |
| KBr | 119 | 4.9E−07 | 1.5E−06 | 5.9E−02 | 1.8E−01 |
| KI | 166 | 5.0E−07 | 1.5E−06 | 8.3E−02 | 2.5E−01 |
| NaF | 41.99 | 4.9E−05 | 1.5E−04 | 2.1E+00 | 6.2E+00 |
| RbCl | 120.92 | 4.9E−06 | 1.5E−05 | 5.9E−01 | 1.8E+00 |
| $ZrOCl_2$—$8H_2O$ | 178.13 | 4.9E−06 | 1.5E−05 | 8.7E−01 | 2.6E+00 |
| ENERGY SUBSTRATES | | | | | |
| D-Glucose | 180.16 | 6.9E+00 | 2.1E+01 | 1.2E+06 | 3.7E+06 |
| Sodium Pyruvate | 110.04 | 2.0E−01 | 5.9E−01 | 2.2E+04 | 6.5E+04 |
| LIPIDS | | | | | |
| Linoleic Acid | 280.45 | 9.4E−05 | 2.8E−04 | 2.6E+01 | 7.9E+01 |
| Lipoic Acid | 206.33 | 2.0E−04 | 7.8E−04 | 4.1E+01 | 1.6E+02 |
| Arachidonic Acid | 304.47 | 6.5E−06 | 1.9E−05 | 2.0E+00 | 5.9E+00 |
| Cholesterol | 386.65 | 5.6E−04 | 1.7E−03 | 2.2E+02 | 6.5E+02 |
| DL-alpha tocopherol-acetate | 472.74 | 1.5E−04 | 4.4E−04 | 6.9E+01 | 2.1E+02 |
| Linolenic Acid | 278.43 | 3.5E−05 | 1.0E−04 | 9.7E+00 | 2.9E+01 |
| Myristic Acid | 228.37 | 4.3E−05 | 1.3E−04 | 9.8E+00 | 2.9E+01 |
| Oleic Acid | 282.46 | 3.5E−05 | 1.0E−04 | 9.8E+00 | 2.9E+01 |
| Palmitic Acid | 256.42 | 3.8E−05 | 1.1E−04 | 9.8E+00 | 2.9E+01 |
| Palmitoleic acid | 254.408 | 3.9E−05 | 1.2E−04 | 9.8E+00 | 2.9E+01 |
| Stearic Acid | 284.48 | 3.4E−05 | 1.0E−04 | 9.8E+00 | 2.9E+01 |
| AMINO ACIDS | | | | | |
| L-Alanine | 89.09 | 2.5E−02 | 2.1E−01 | 2.2E+03 | 1.8E+04 |
| L-Arginine hydrochloride | 147.2 | 2.7E−01 | 1.5E+00 | 4.0E+04 | 2.2E+05 |
| L-Asparagine-$H_2O$ | 150.13 | 5.0E−02 | 2.1E−01 | 7.5E+03 | 3.1E+04 |
| L-Aspartic acid | 133.1 | 2.5E−02 | 2.1E−01 | 3.3E+03 | 2.7E+04 |
| L-Cysteine-HCl-$H_2O$ | 175.63 | 3.9E−02 | 1.2E−01 | 6.9E+03 | 2.1E+04 |
| L-Cystine dihydrochloride | 313.22 | 3.9E−02 | 1.2E−01 | 1.2E+04 | 3.7E+04 |
| L-Glutamic acid | 147.13 | 2.5E−02 | 2.1E−01 | 3.7E+03 | 3.0E+04 |
| L-Glutamine | 146.15 | 1.5E+00 | 4.4E+00 | 2.1E+05 | 6.4E+05 |

TABLE 1-continued

| Ingredient | molar mass (g/mol) | Min. Conc. (mM) | Max. Conc. (mM) | Min. Conc. (ng/mL) | Max. Conc. (ng/mL) |
|---|---|---|---|---|---|
| Glycine | 75.07 | 1.5E−01 | 4.4E−01 | 1.1E+04 | 3.3E+04 |
| L-Histidine monohydrochloride monohydrate | 209.63 | 5.9E−02 | 1.8E−01 | 1.2E+04 | 3.7E+04 |
| L-Isoleucine | 131.17 | 1.6E−01 | 4.9E−01 | 2.1E+04 | 6.4E+04 |
| L-Leucine | 131.17 | 1.8E−01 | 5.3E−01 | 2.3E+04 | 7.0E+04 |
| L-Lysine hydrochloride | 182.65 | 2.0E−01 | 5.9E−01 | 3.6E+04 | 1.1E+05 |
| L-Methionine | 149.21 | 4.5E−02 | 1.4E−01 | 6.8E+03 | 2.0E+04 |
| L-Phenylalanine | 165.19 | 8.5E−02 | 2.5E−01 | 1.4E+04 | 4.2E+04 |
| L-Proline | 115.13 | 1.1E−01 | 3.2E−01 | 1.2E+04 | 3.7E+04 |
| L-Serine | 105.09 | 1.5E−01 | 4.4E−01 | 1.5E+04 | 4.6E+04 |
| L-Threonine | 119.12 | 1.8E−01 | 5.3E−01 | 2.1E+04 | 6.3E+04 |
| L-Tryptophan | 204.23 | 1.7E−02 | 5.2E−02 | 3.5E+03 | 1.1E+04 |
| L-Tyrosine disodium salt hydrate | 225.15 | 8.4E−02 | 3.7E−01 | 1.9E+04 | 8.4E+04 |
| L-Valine | 117.15 | 1.8E−01 | 5.3E−01 | 2.1E+04 | 6.2E+04 |
| VITAMINS | | | | | |
| Ascorbic acid | 176.12 | 1.3E−01 | 3.8E−01 | 2.2E+04 | 6.7E+04 |
| Biotin | 244.31 | 5.6E−06 | 1.7E−05 | 1.4E+00 | 4.1E+00 |
| $B_{12}$ | 1355.37 | 2.0E−04 | 5.9E−04 | 2.7E+02 | 8.0E+02 |
| Choline chloride | 139.62 | 2.5E−02 | 7.5E−02 | 3.5E+03 | 1.1E+04 |
| D-Calcium pantothenate | 238.27 | 1.8E−03 | 1.4E−02 | 4.4E+02 | 3.4E+03 |
| Folic acid | 441.4 | 2.4E−03 | 7.1E−03 | 1.0E+03 | 3.1E+03 |
| i-Inositol | 180.16 | 2.7E−02 | 1.1E−01 | 4.9E+03 | 1.9E+04 |
| Niacinamide | 122.12 | 6.5E−03 | 2.0E−02 | 7.9E+02 | 2.4E+03 |
| Pyridoxine hydrochloride | 205.64 | 3.8E−03 | 1.1E−02 | 7.8E+02 | 2.4E+03 |
| Riboflavin | 376.36 | 2.3E−04 | 6.8E−04 | 8.6E+01 | 2.6E+02 |
| Thiamine hydrochloride | 337.27 | 3.3E−03 | 3.6E−02 | 1.1E+03 | 1.2E+04 |
| GROWTH FACTORS/PROTEINS | | | | | |
| GABA | 103.12 | 0 | 1.5E+00 | 0 | 1.5E+05 |
| Pipecolic Acid | 129 | 0 | 1.5E−03 | 0 | 1.9E+02 |
| bFGF | 18000 | 0 | 2.17E−07 | 0 | 3.9E+00 |
| TGF beta 1 | 25000 | 0 | 3.5E−08 | 0 | 8.8E−01 |
| Human Insulin | 5808 | 0 | 5.9E−03 | 0 | 3.4E+04 |
| Human Holo-Transferrin | 78500 | 0 | 2.1E−04 | 0 | 1.6E+04 |
| Human Serum Albumin | 67000 | 0 | 2.9E−01 | 0 | 2.0E+07 |
| Glutathione (reduced) | 307.32 | 0 | 9.6E−03 | 0 | 2.9E+03 |
| OTHER COMPONENTS | | | | | |
| Hypoxanthine Na | 136.11 | 5.9E−03 | 2.6E−02 | 8.0E+02 | 3.6E+03 |
| Phenol red | 354.38 | 8.5E−03 | 2.5E−02 | 3.0E+03 | 9.0E+03 |
| Putrescine-2HCl | 161.07 | 2.0E−04 | 5.9E−04 | 3.2E+01 | 9.5E+01 |
| Thymidine | 242.229 | 5.9E−04 | 1.8E−03 | 1.4E+02 | 4.3E+02 |
| 2-mercaptoethanol | 78.13 | 4.9E−02 | 1.5E−01 | 3.8E+03 | 1.1E+04 |
| Pluronic F-68 | 8400 | 1.2E−02 | 3.5E−02 | 9.8E+04 | 2.9E+05 |
| Tween 80 | 1310 | 1.6E−04 | 4.9E−04 | 2.2E+02 | 6.5E+02 |

The liquid phase of the cell culture medium may be water, serum, or albumin.

Many of the ingredients or components listed above in Table 1 are not necessary, or can be used in lower concentrations.

It is contemplated that the cell culture medium may contain insulin or an insulin substitute. Similarly, the cell culture medium may contain transferring or a transferring substitute. However, in more specific embodiments, it is contemplated that the cell culture medium may not contain (1) insulin or insulin substitute, or (2) transferring or transferring substitute, or any combination of these two components.

It should be noted that other cell culture media may contain growth factors such as interleukin-1 beta (IL-1β or catabolin), interleukin-6 (IL6), or pigment epithelium derived factor (PEDF). Such growth factors may not be present in the cell culture medium of the present disclosure.

One specific cell culture medium that may be used is a basal medium. Basal medium is an unsupplemented medium that promotes the growth of many types of microorganisms, which do not require any special nutrient supplements. In particular embodiments, the basal medium is Keratinocytes Growth Medium—Chemically Defined (KGM-CD) basal medium commercially available from Lonza.

The basal medium may include insulin and growth supplement. The insulin may be recombinant human insulin. Additional ingredients present in the basal medium can include human epidermal growth factor (hEGF); hydrocortisone; antibiotics and/or antifungals such as gentamicin or amphotericin B; and growth hormones such as epinephrine and transferring.

The systems containing either a LN-421 or a LN-511 substrate and basal medium work extremely well for supporting keratinocytes in a completely chemically defined environment and xeno-free conditions without feeder cells or animal serum or any inhibitors of apoptosis. Examples of feeder cells include mouse fibroblasts or human dermal fibroblasts.

It is contemplated that the cell culture medium will be completely defined and xeno-free. The medium should also be devoid of any differentiation inhibitors, differentiation inductors, or apoptosis inhibitors, or animal serum. Examples of differentiation inductors include Noggin or keratinocyte growth factor.

The combination of the laminin substrate with the cell culture medium of the present disclosure results in a cell culture system that can efficiently support human keratinocytes. Essentially all that is required is a laminin and a minimal amount of nutrition. It is particularly contemplated that the laminin used in combination with this cell culture medium is either LN-511 or LN-421.

The cell culture system in some embodiments includes at least one of LN-411, LN-421, LN-511, or LN-521 in the substrate and maintains human keratinocytes longer than shown by conventional methods using feeder cells and animal serum.

The following examples are for purposes of further illustrating the present disclosure. The examples are merely illustrative and are not intended to limit devices made in accordance with the disclosure to the materials, conditions, or process parameters set forth therein.

EXAMPLES

Primary Keratinocyte Isolation

Human epidermal keratinocytes (HEK) were isolated from surgical waste from plastic surgery operations of healthy subjects, with informed consent from these donors and ethics approval from the ethics committee of Singapore General Hospital. Briefly, a maximum of 4 $cm^2$ tissue was washed in phosphate buffered saline (PBS) (Lonza) and incubated in 10 mL of 2.5 mg/mL Dispase II (Roche) in Dulbecco's Modified Eagle Medium (DMEM) (Gibco) and left overnight at 4° C. The following day, epidermis was mechanically separated from dermis with fine forceps and incubated in 0.05% trypsin-EDTA solution (Gibco) for 15 minutes at 37° C. Upon cellular dissociation, trypsin activity was reduced by diluting the solution with three volumes of fresh DMEM (Gibco). Keratinocytes were then collected through centrifugation and resuspended in Keratinocytes Growth Medium—Chemically Defined (KGM-CD) (Lonza).

Primary Keratinocyte Culture 6-well tissue culture plates (Corning, Costar) were coated overnight at 4° C. with sterile LN-111, LN-332, LN-411, LN-421, LN-511 or LN-521 (BioLamina AB) at 2.5 µg/$cm^2$. Freshly isolated human epidermal keratinocytes were seeded on pre-coated plates initially at a density of 9×$10^4$/$cm^2$ and cultured in KGM-CD (Lonza) at 37° C., 10% $CO_2$. For control plates, human epidermal keratinocytes were either cultured according to the method of Rheinwald & Green, or were cultured on non-coated plates. Briefly, freshly isolated HEKs (9×$10^4$/$cm^2$) were cultured on a feeder layer of lethally irradiated (60 Gy) 3T3-J2 fibroblasts in complete FAD medium: DMEM (Gibco) and Ham's F12 (Gibco) media (3:1 ratio) supplemented with 10% fetal bovine serum (FBS) (Hyclone), 5 µg/mL insulin (Insulatard®), 0.18 mM adenine (Calbiochem), 0.4 µg/mL hydrocortisone (Calbiochem), 2 nM triiodothyronine (Sigma), 0.1 nM cholera toxin (Sigma), 10 ng/mL epidermal growth factor (Upstate), and 100 IU/mL—100 µg/mL penicillin-streptomycin (Gibco). Upon confluency, HEK cultures in the serum-free system were trypsinized using TrypLE Select (Gibco Invitrogen) for 8-16 minutes at 37° C., while HEK cultures on control plates were trypsinized with 0.05% trypsin-EDTA (Gibco) for 5 minutes at 37° C. Subconfluent primary cultures were serially passaged at 1×$10^4$ cells/$cm^2$. The number of cumulative population doublings was calculated using the following formula: PD=(log N/N0)/log2, where N represents the total number of cells obtained at each passage and N0 represents the number of cells plated at the start of the experiment.

Quantitative PCR Analysis

Total RNA from HEK cells at different passages was purified using RNeasy Micro Kit (Qiagen) according to the manufacturer's instructions. The yield was determined by NanoDrop ND-2000 spectrophotometer (NanoDrop Technologies). For quantitative RT-PCR analysis, cDNA was synthesized from 500 ng of total RNA in a 20 µL reaction mixture using TaqMan Reverse Transcription Reagents Kit (Applied BioSystems) according to the manufacturer's instructions. Real-time quantitative RT-PCR was performed with synthesized cDNA in assay mix containing iQ SYBR Green Super mix (BioRad) and primers for genes of interest. GAPDH was used as the normalizing control.

FACS Analysis

Cells were collected at different passages and single-cell suspensions were fixed with Fixation Reagent (Medium A; Life Technologies) for 15 minutes at room temperature, washed with FACS buffer (0.5% BSA, 2 mM EDTA in 1× PBS), blocked with 5% goat serum in FACS buffer, immunostained with primary antibodies in Permeabilization Reagent (Medium B; Life Technologies) for 15 minutes at room temperature, and detected with secondary antibodies diluted in 1% goat serum in FACS buffer. For fluorophore-conjugated antibodies, fixed cells were incubated with antibodies diluted in Medium B and human FcR blocking reagent (Miltenyi Biotec, 1:50) for 30 minutes at room temperature. Stained cells were resuspended in FACS buffer and subjected to FACS analysis (MACSQuant VYB, Miltenyi Biotec). Data were analyzed using MACSQuantify (Miltenyi Biotec) software.

Organotypic Culture

Epidermis of glycerol-preserved allogeneic skin (EURO SKIN BANK, EA Beverwijk, Netherland) was removed mechanically after several cycles of snap-freezing and thawing. This de-epidermalized dermis (DED) was then cut into 2×2 cm squares and the reticular side of the dermis was seeded with 5×$10^5$ human dermal fibroblast with the help of a 1 cm diameter stainless steel ring. The next day, each DED was flipped and 2×$10^5$ HEK cells that had been grown on either laminin or with R&G systems were seeded separately on individual DED in CFAD medium for 7 days. Subsequently, cultures were lifted to an air-liquid interface for 14 days to stratify. Each sample was then processed for cryosectioning and stained with H&E staining.

Generation of RNA-Sequencing (RNA-Seq) Data

Adult patient-derived keratinocytes were grown separately either in 3T3 co-cultures (n=2), or on LN-421 (n=4) or LN-511 (n=3) coatings. In addition, whole skin was also isolated (n=3). RNA was isolated from either culture plates or whole skin with microRNA purification kit (Norgen Biotek Corporation) according to manufacturer's guidelines. RNAseq libraries were prepared using Illumina Tru-Seq Stranded Total RNA with Ribo-Zero Gold kit protocol, according to the manufacturer's instructions (Illumina, San Diego, Calif., USA). Libraries were validated with an Agilent Bioanalyzer (Agilent Technologies, Palo Alto, Calif.), diluted and applied to an Illumina flow cell using the Illumina Cluster Station. Sequencing was performed on Illumina HiSeq2000 sequencer at the Duke-NUS Genome Biology Facility with the paired-end 100 by read option.

RNA-seq reads were assessed for quality and aligned to hg38 (Ensembl Gene annotation build 79) using STAR 2.5.2b and quantified using RSEM 1.2.31. 43 million reads mapped on average in the cultured samples and 113.3 million on average in the samples from whole skin were obtained. Gene annotation was retrieved from Ensembl version 79 (hg38) using the R library biomaRt 2.30.0. Ribosomal genes (Ensembl gene biotype "rRNA") and mitochondrial genes were removed (584 genes in total). Small non-coding RNA genes "RN7SL1" and "RN7SL2" were removed, as due to their high expression levels, they were outliers in the gene expression distribution. Gene counts were rounded using the R function round. A pre-filtering step was added in which only genes with more than 1 count were kept when summing up across all samples.

RNA-Seq Data Analysis

Differential expression analysis and functional enrichment was used to compare the three culturing methods: 3T3 co-culture, LN-421 and LN-511. Differential expression analysis was carried out with DESeq2 1.14.1. DESeq2 was run pairwise using Wald test, collapsing technical replicates and adjusting for patient effects (i.e. the covariate "Patient_ID" was added in the model). Three pairwise comparisons were carried out, LN-421 samples were compared against 3T3, LN-511 against 3T3 and LN-511 against LN-421. In the DESeq2 results function, the alpha parameter was set to 0.05, the rest of parameters were left as default. Genes were considered significantly differentially expressed (DE) if Benjamini & Hochberg (BH) adjusted p-value <0.05.

Functional enrichment analysis of the differential expression results was performed with Gene Set Enrichment Analysis (GSEA) software 2-2.2.2. All genes included in DESeq2 output were mapped to HGNC symbols and ranked by the corresponding DESeq2 output Wald statistic (i.e. the estimate of the log2 fold change divided by its standard error). GSEA was run assessing overrepresentation of Hallmark gene sets (i.e. coherently expressed gene signatures derived from the aggregation of groups of annotated gene sets that represent well-defined biological states or processes). Hallmark gene sets were obtained from the Molecular Signatures Database gene sets 5.1. GSEA was run in classic pre-rank mode with 10,000 permutations to assess the false discovery rate (FDR). In the GSEA runs, maximum gene set size was set to 5,000 and minimum cluster size was set to 10. Gene sets were considered enriched if FDR<0.05.

Visualization of Expression Levels of Selected Genes

Transcripts Per Million (TPM) were pre-filtered by removing lowly expressed genes (i.e. TPMs were summed up across all samples and only genes with TPM higher than one were kept). TPM levels were logged (after adding and offset of 1) and adjusted for patient effects using the function removeBatchEffect from the R library limma 3.30.13.

Preparation of Cultured Epidermal Skin Equivalent

Transparent fibrin mats were prepared in a laminar hood using 2 mL or 5 mL TISSEEL kit (Baxter). Fibrinogen from the kit was diluted two times above the recommended reconstitution using 1.1% sodium chloride solution (NaCl) containing 1 mM of calcium chloride ($CaCl_2$); this solution was subsequently mixed in equal volume with thrombin provided by the kit, and diluted to 3 IU/mL using 1.1% NaCl and 1 mM $CaCl_2$ solution. The above mixed solutions were dispensed uniformly in 10×10 $cm^2$ dishes, left at room temperature for 10 to 15 minutes for complete polymerization, and stored at 4° C. until use. To prevent fibrinolysis during the culture of HEKs on the fibrin mat, aprotinin (Trasylol, Bayer) was added to a final concentration of 150 kIU/mL in the culture medium at each feeding. For transplantation, fibrin mats were either coated with 2.5 μg/$cm^2$ LN-511 or LN-421 and incubated at 4° C. overnight, or seeded with lethally γ-irradiated 3T3-J2 fibroblasts and incubated at 37° C. overnight. HEKs were then seeded the next day at 10,000 cells/$cm^2$ and grown to confluence. On the day of surgery, all grafts were washed twice with respective serum-free medium (KGM-CD for laminin samples and fresh DMEM for 3T3 co-culture sample).

Transplantation of Human Epidermal Grafts onto Nude Mice

Animal studies were carried out with an approved protocol from SingHealth Institutional Animal Care and Use Committee (IACUC). Eight to ten week-old nude athymic BALB/c nu/nu mice were purchased from Animal Resource Centre (ARC, Perth, Western Australia) and used as skin graft recipients. Mice were housed and maintained in SingHealth Experimental Medical Center (SEMC) under specific pathogen-free conditions. All mice were acclimated to their environment for at least 1 week prior to the experimental procedure.

On the day of surgery, mice were treated with buprenorphine (1 mg/kg) twice, beginning in the morning (or at least one hour before the surgery) and another time at the end of the day. In a laminar flow hood, mice were individually anesthetized using 5% isoflurane in a chamber. For maintenance, the mice were subjected to 2% isoflurane via inhalation through a mask for the surgical procedure. Flap procedure was done following the method developed by Barrandon et al., *J. Investigative Dermatology*, 91, 315-318 (1988). Briefly, dorsal skin surfaces of the mice were aseptically cleansed twice with alcohol swabs. A rectangular flap of 2×2 $cm^2$ were incised with scissors and lifted. A sheet of Safetac foam (Mepilex Lite dressing), slightly larger than the flap, was inserted under the animal skin with the sticky side facing down. Subsequently, cultured human epidermal skin equivalent on fibrin (exposed cell surface down) were placed on the Mepilex dressing with two layers of inert Silon-TSR dressing inserted in between to protect the cells. After moistening the graft with a drop of serum free medium, flap was folded back in place over the graft and incision closed with non-absorbable 6-0 sutures to protect and fix the graft in place.

To harvest the graft, the animal was sacrificed with $CO_2$ inhalation. The graft was then harvested and either fixed in 4% buffered paraformaldehyde and paraffin-embedded, or snap-frozen in liquid nitrogen. 5 μm sections were then collected and processed for either haematoxylin and eosin staining or immunostaining.

Statistical Analyses of the Experimental Data

Data are presented as means±SEM from 3 to 7 different patient samples. Differences in relative mRNA expression and surface marker protein expression at different time points were assessed with one-way ANOVA, corrected for multiple comparisons using Tukey's post hoc test. All graphs and statistical analyses were generated by Prism Software 7.0 (GraphPad). Differences were regarded as significant at p <0.05.

General Tissue Culture Methods

Twelve-well tissue culture plates (Costar) were coated overnight at 4° C. with sterile LN-411, LN-421, LN-511, and LN-521 at densities of 2 μg/$cm^2$ according to the laminin manufacturer's instructions (BioLamina AB). In other cases, 6-well tissue culture plates (Corning, Costar) were coated overnight at 4° C. with sterile LN-111, LN-332, LN-411, LN-421, LN-511 or LN-521 (BioLamina AB) at 2.5 μg/$cm^2$.

Human epidermal keratinocyte samples were washed in phosphate buffered saline (PBS) and incubated in 10 mL of 2.5 mg/mL Dispase II (Roche) in DMEM (Gibco) overnight at 4° C. The following day, epidermis was mechanically separated from dermis with fine forceps and incubated in 0.05% trypsin-EDTA (Gibco) at 37° C. for 15 minutes. Upon cellular dissociation, trypsin activity was reduced by diluting the solution with three volumes of fresh DMEM. Keratinocytes were then collected through centrifugation and resuspended in Keratinocytes Growth Medium—Chemically Defined (KGM-CD, Lonza).

Freshly isolated human epidermal keratinocytes were seeded on pre-coated plates (and control plates) initially at densities of $0.9 \times 10^5$ to $1 \times 10^5$ cells/cm$^2$ and cultured at 37° C., 10% $CO_2$ in KGM-CD.

For control plates, human epidermal keratinocytes were either cultured according to the method of Rheinwald & Green, or cultured on non-coated plates. Briefly, freshly isolated HEKs ($9 \times 10^4$/cm$^2$) were cultured on a feeder layer of lethally irradiated (60 Gy) 3T3-J2 fibroblasts in complete FAD medium: DMEM (Gibco) and Ham's F12 (Gibco) media (3:1 ratio) supplemented with 10% fetal bovine serum (FBS) (Hyclone), 5 µg/mL insulin (Insulatard®), 0.18 mM adenine (Calbiochem), 0.4 µg/mL hydrocortisone (Calbiochem), 2 nM triiodothyronine (Sigma), 0.1 nM cholera toxin (Sigma), 10 ng/mL epidermal growth factor (Upstate), and 100 IU/mL—100 µg/mL penicillin-streptomycin (Gibco).

Upon confluency, the cells were trypsinized by using TrypLESelect (Gibco Invitrogen) for 8-16 minutes at 37° C. Subsequently, the keratinocytes were routinely passaged at densities of $1 \times 10^4$ cells/cm$^2$. The number of cumulative population doublings was calculated using the following formula: PD=(log N/N0)/log2, where N represents the total number of cells obtained at each passage and N0 represents the number of cells plated at the start of the experiment.

Example 1

Human skin samples were obtained from donors with consent from Singapore General Hospital. Briefly, samples were embedded in OCT medium, cryosectioned at 5 µm (micrometer) sections and subjected to individual laminin isoform immunofluorescent staining and counterstained with DAPI.

Laminin isoform stainings at human skin basement membrane showed positive for laminin alpha1, alpha3, alpha5, beta1, beta2, beta3, gamma1, and gamma2 isoforms. Laminin alpha2 and alpha4 isoforms were not present on basement membrane, but laminin alpha4 stained positive on blood vessels. Laminin gamma3 isoform showed non-specific staining. These results show that LN-332, LN-511, and LN-521 were expressed in the sub-epidermal basement membrane.

Example 2

Next, the mRNA expression level of the laminin isoforms expressed in skin dermatome section was obtained through real-time PCR. Laminin alpha3, alpha5, beta1, beta2, beta3, beta4, gamma1, and gamma2 isoforms were positively expressed.

Example 3

Freshly isolated human epidermal keratinocytes prepared using the method above were cultured on laminin substrates (LN-332, LN-411, LN-421, LN-511, LN-521). LN-111 substrate and a tissue culture dish without any laminin coating served as negative controls. Keratinocytes co-cultured with 3T3 fibroblasts were used as a positive control. Cells were then cultured in KGM-CD basal medium. All HEK cultures on laminins was carried out in an animal-free and defined KGM-CD cell culture system without any initial expansion using Rheinwald & Green's 3T3 feeder layer.

As shown in FIGS. 1A-1J, human keratinocytes cultured on LN-411, LN-421, LN-511, or LN-521 fared better compared to those keratinocytes cultured on control substrates. Cells cultured on negative control (No coating), LN-111, and LN-332 did not survive. On the contrary, keratinocytes could attach and proliferate on LN-411, LN-421, LN-511, and LN-521, as well as the positive control (3T3). Keratinocytes cultured on LN-411 and LN-421 formed colonies, while those that were cultured on LN-511 and LN-521 appeared to attach and grow as individual entities. Keratinocytes cultured in combination of both LN-421 and LN-511 grew well.

Figure 2B:
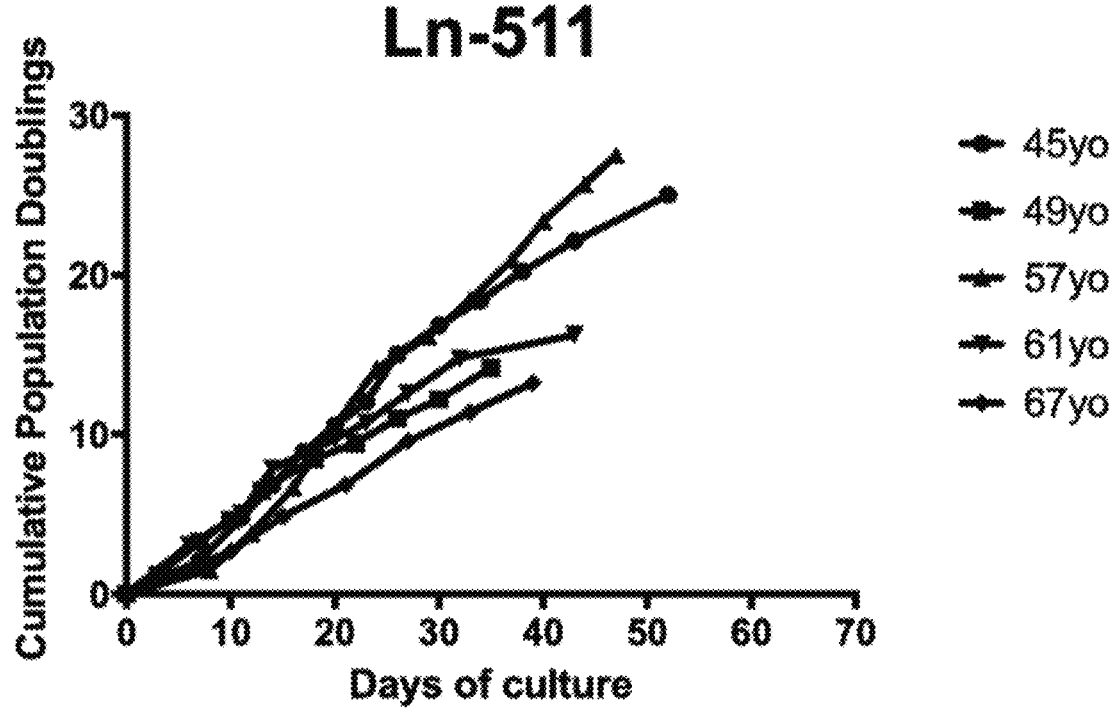
Figure 2C:
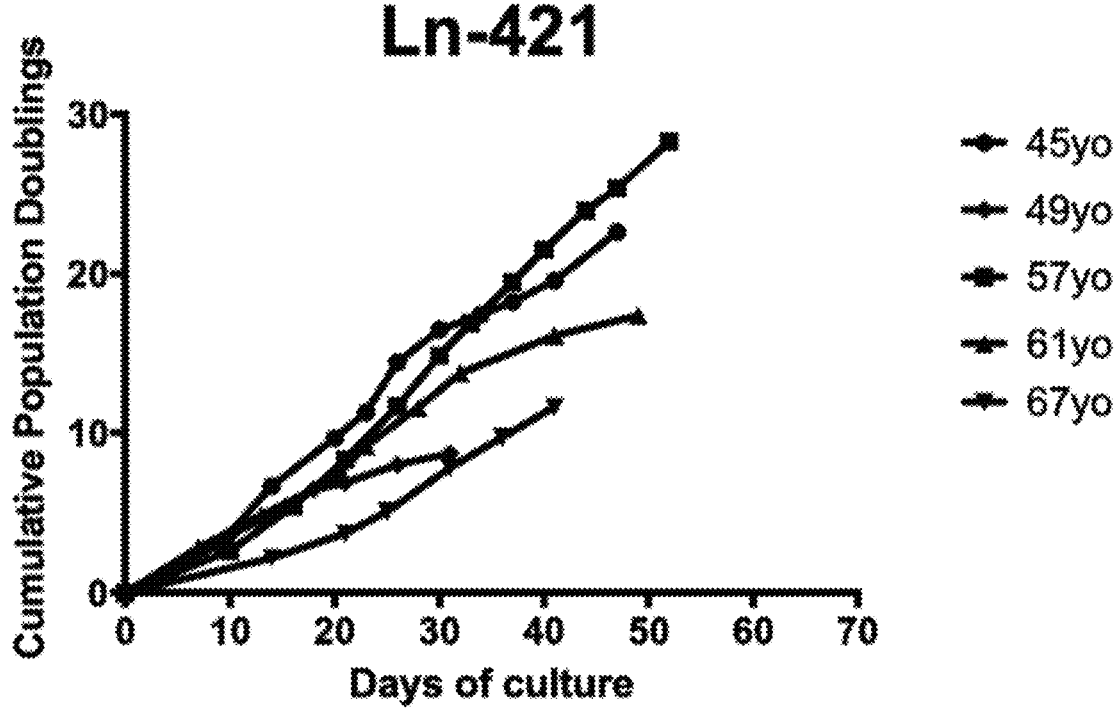
Figure 2D:
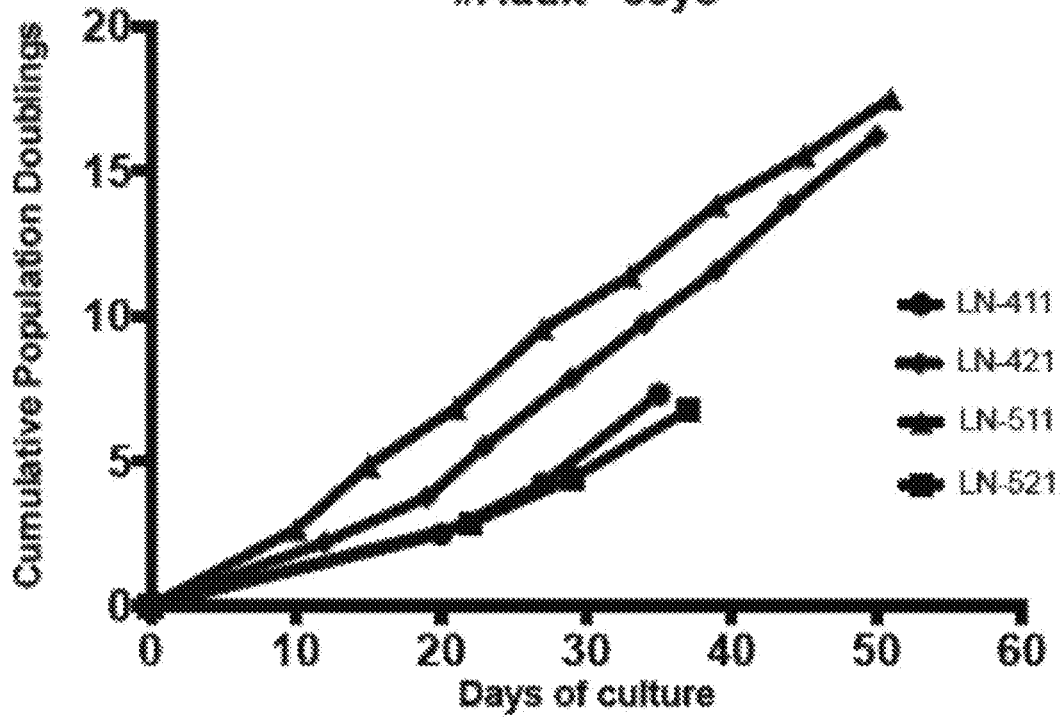
Figure 3A:
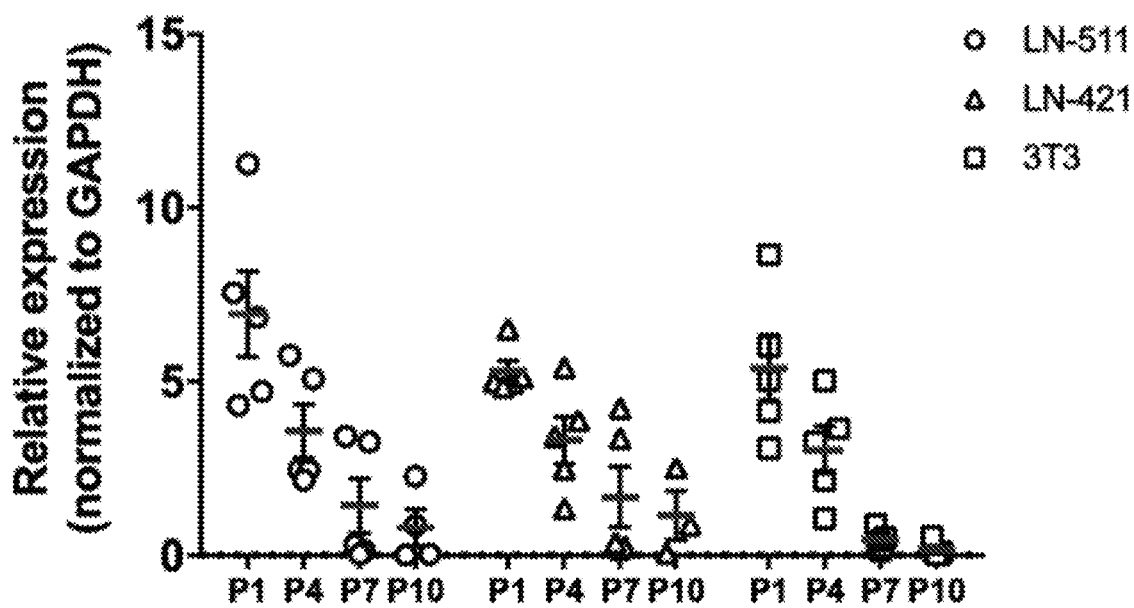
FIGS. 3A-3D are a set of graphs showing the time dependent qPCR expression profile of keratinocyte progenitor cell and differentiation markers. Keratinocytes were cultured on a laminin-coated system or co-cultured with 3T3. Upon confluency, cells were harvested and RNA was isolated for qPCR analysis. Each graph plots the mRNA relative expression of the marker, normalized to GAPDH over ten passages. The circles are for LN-511, the triangles are for LN-421, and the squares are for 3T3. The values are indicated for passages 1 (P1), 4 (P4), 7 (P7), and 10 (P10).
Figure 3B:
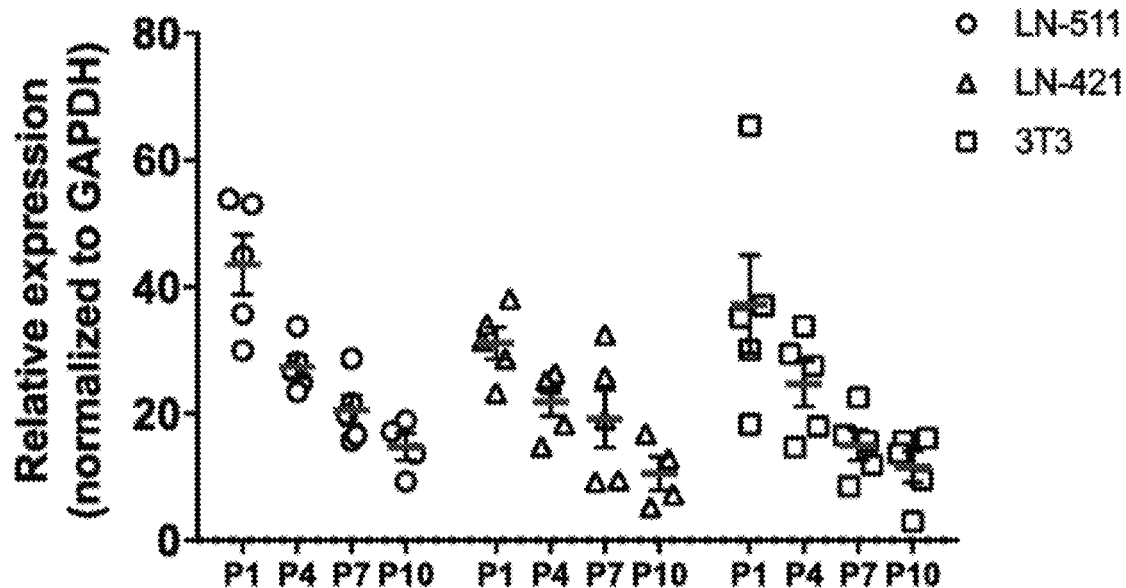
Figure 3C:
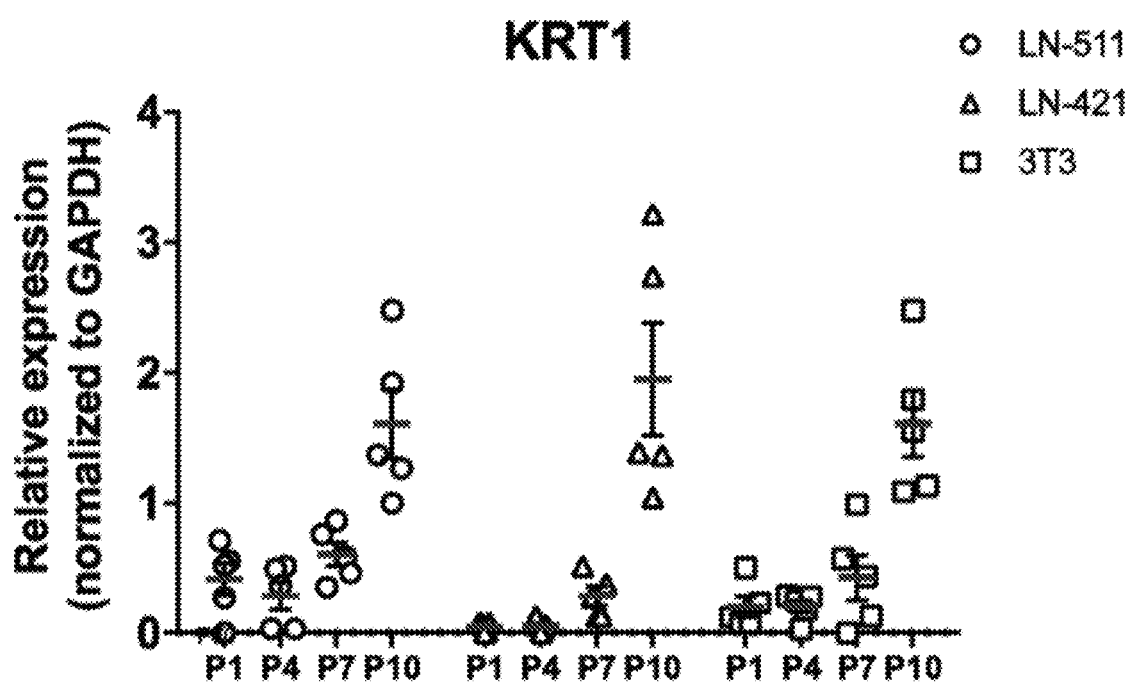
Figure 3D:
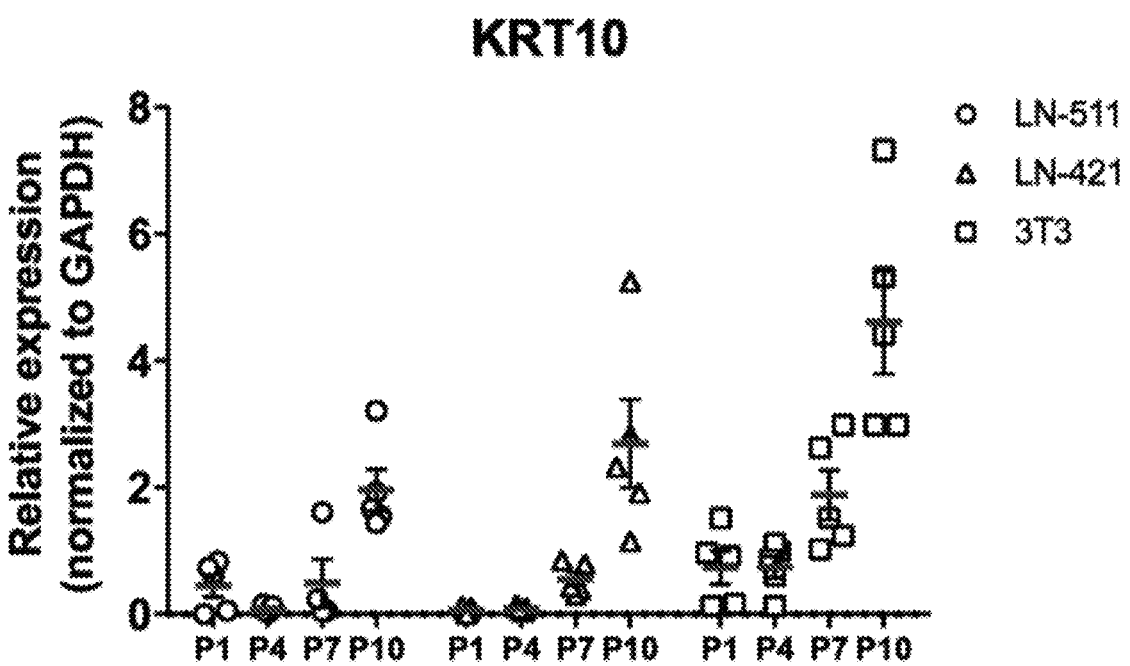

Keratinocytes were counted, and the growth rates of keratinocytes cultured on LN-511, LN-421, and the positive control were graphed as shown in FIGS. 2A-2C. Population doubling was calculated as PD=3.32×µg(number of cells harvested/number of cells seeded). These graphs show that LN-511 and LN-421 were able to support keratinocyte proliferation and colony forming capabilities. Individually, LN-511 and LN-421 were better able to sustain keratinocytes in long term culture compared to LN-521 and LN-411. This is reflected in FIG. 2D in their respective cumulative population doublings.

Example 4

To examine the genetic stability of keratinocytes cultured on LN-511 and LN-421, karyotyping of keratinocytes was carried out at early (Passage 1) and prolonged culture (Passage 9). Keratinocytes co-cultured with 3T3 was used as control in respective passages. Keratinocytes cultured on LN-511 and LN-421 in both passage 1 and passage 9 showed normal karyotyping with no observable translocations or chromosomal changes present.

Example 5

Quantitative polymerase chain reaction (qPCR) was performed on human epidermal keratinocytes plated on laminin substrates of either LN-511 or LN-421. qPCR was conducted at passage 1, passage 4, passage 7, and passage 10 to observe expression profiles of keratinocyte progenitor markers (KRT5, KRT14) and differentiation makers (KRT1, KRT10), compared to the 3T3 control substrate.

As shown in FIGS. 3A-3D, qPCR expression profiles of progenitors' and differentiation markers' relative expressions were normalized to GAPDH over ten passages. Overall, the expression profile for each basal/differentiation marker of keratinocytes cultured on either LN-511 (circles) or LN-421 (triangles) showed a similar trend with the control substrate (3T3, squares). In the early passages, keratinocytes grown on both LN-511 and LN-421 highly expressed KRT5 and KRT14. The onset of differentiation markers expression began after passage 7, where KRT1 and KRT10 gradually increased.

Figure 4A:
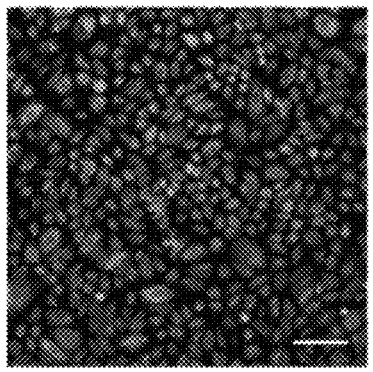
FIGS. 4A-4N are a set of immunofluorescent images of keratinocyte progenitor markers (KRT5, KRT14, KRT15, p63) and differentiation markers (IVL, KRT1, KRT10). Keratinocytes were cultured on substrates coated with either LN-511 or LN-421. At early passage (P1), the cells were fixed and immunostained with specific keratinocytes markers and counterstained with DAPI. Keratinocytes at early passage (P1) expressed normal basal cell markers (KRT5 and KRT14) and low differentiation markers (KRT1 and KRT10).
Figure 4B:
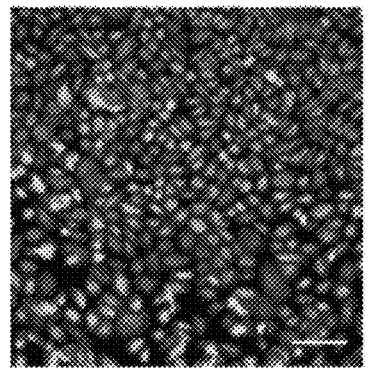
FIG. 4B is LN-511, for KRT14.
Figure 4C:
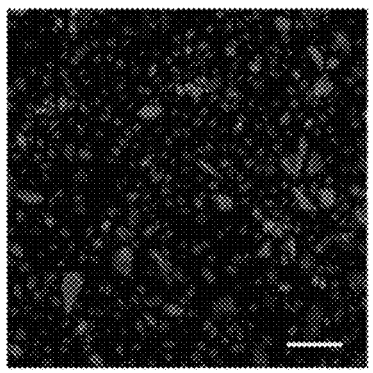
FIG. 4C is LN-511, for KRT15.
Figure 4D:
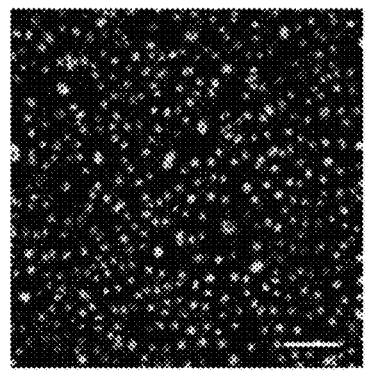
FIG. 4D is LN-511, for p63.
Figure 4E:
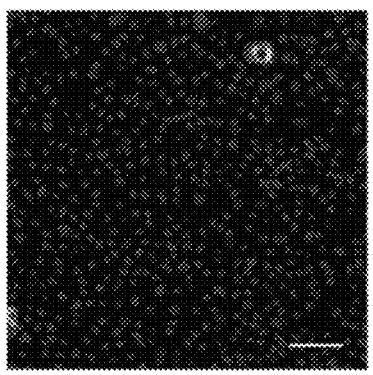
FIG. 4E is LN-511, for IVL.
Figure 4F:
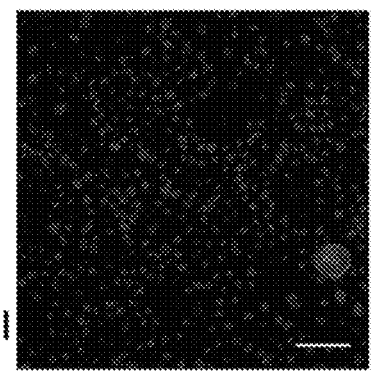
FIG. 4F is LN-511, for KRT10.
Figure 4G:
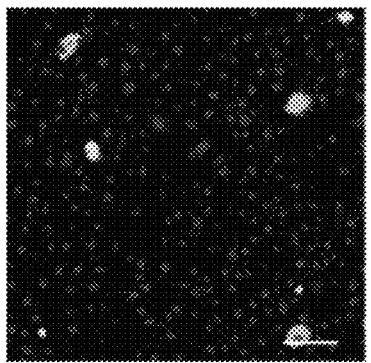
FIG. 4G is LN-511, for KRT1.
Figure 4H:
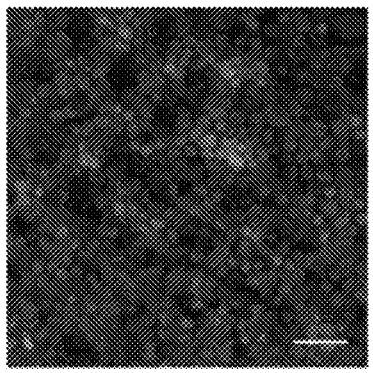
FIG. 4H is LN-421, for KRT5.
Figure 4I:
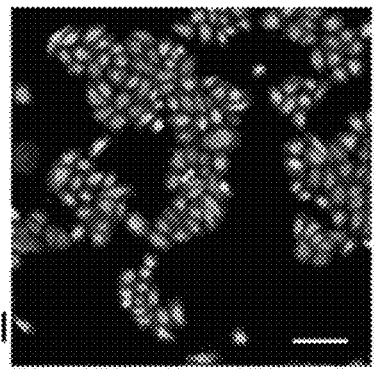
FIG. 4I is LN-421, for KRT14.
Figure 4J:
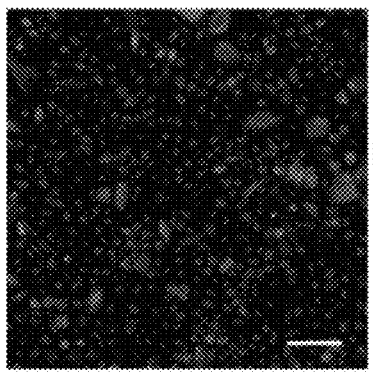
FIG. 4J is LN-421, for KRT15.
Figure 4K:
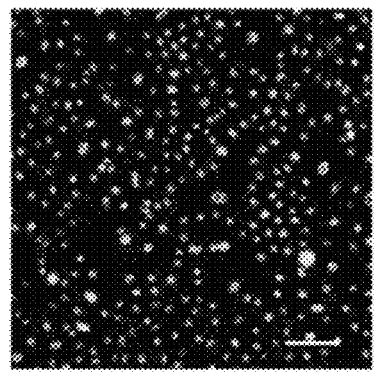
FIG. 4K is LN-421, for p63.
Figure 4L:
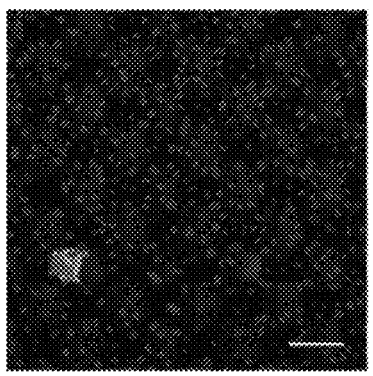
FIG. 4L is LN-421, for IVL.
Figure 4M:
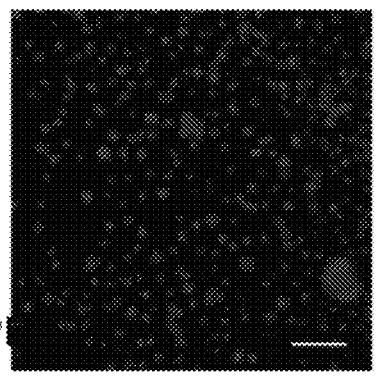
FIG. 4M is LN-421, for KRT10.
Figure 4N:
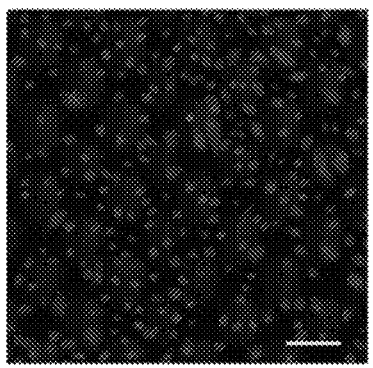

On early passage (P1), cells cultured on LN-511 or LN-421 substrate were fixed and immunostained with specific keratinocyte markers and counterstained with DAPI. These are seen in FIGS. 4A-4N. Keratinocytes at early passage (P1) expressed normal basal cell markers (KRT5, KRT14, KRT15, p63) and low differentiation markers (IVL, KRT10, KRT1).

Example 4

After reaching confluency, cells were collected and subjected for fluorescence-activated cell sorting (FACS) analysis for progenitor markers (KRT5, KRT14, ITGA6, ITGB1, and KRT15) or differentiation markers (KRT1, KRT10). This was done for cells plated on laminin substrates of either LN-511 or LN-421 or co-cultured with 3T3-fibroblast feeder cells.

Figure 5:
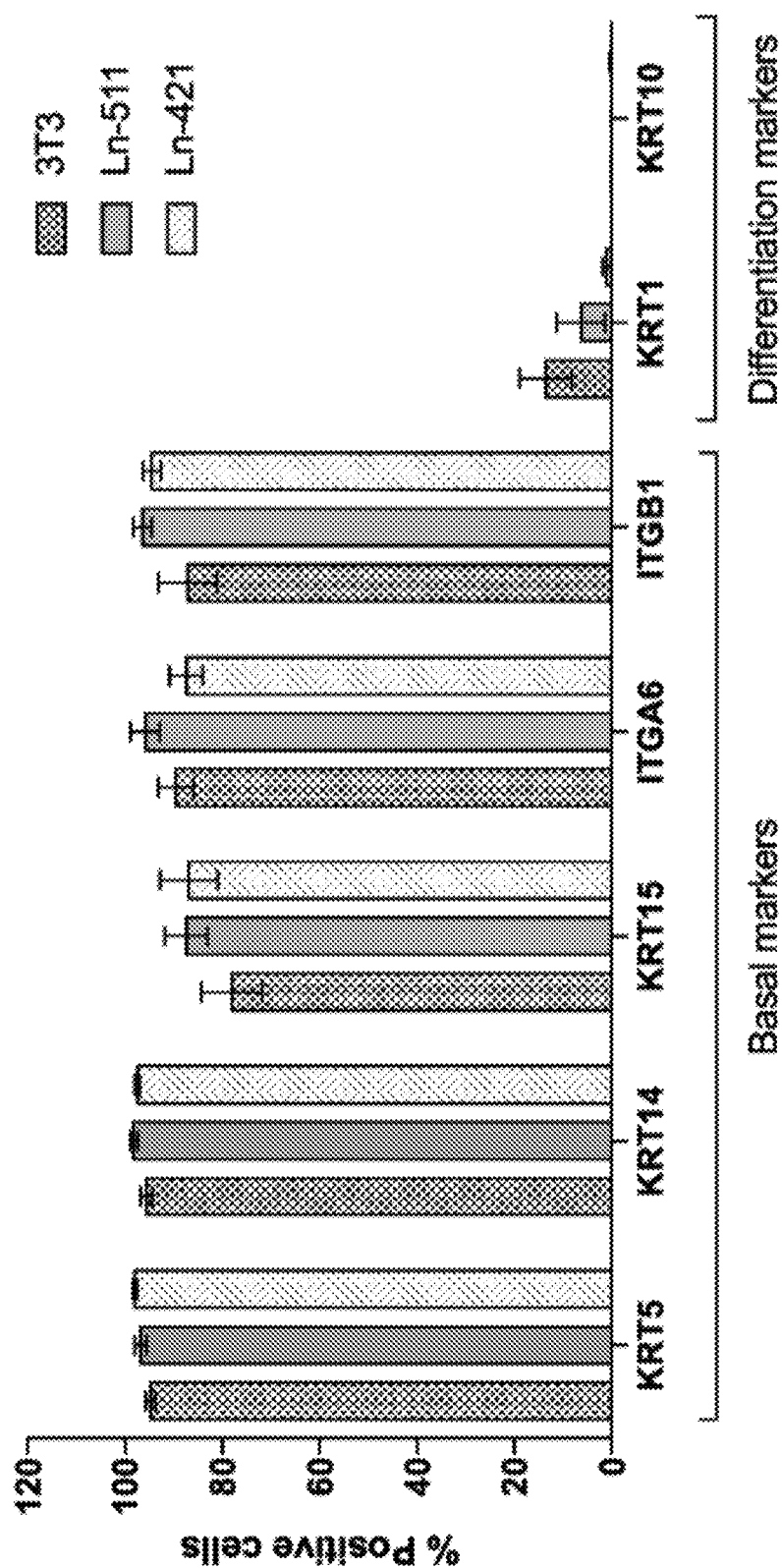
FIG. 5 is a bar graph showing the results. The y-axis indicates the % of positive cells (i.e. expressing the marker), and runs from 0 to 120% in increments of 20%. The markers are indicated on the x-axis, and are, running from left to right, KRT5, KRT14, KRT15, ITGZ6, ITGB1, KRT1, and KRT10. For each marker, the left bar is 3T3 substrate, the center bar is LN-511 substrate, and the right bar is LN-421.

FIG. 5 is a graph showing the results for each marker on each substrate. The FACS analysis showed that keratinocytes cultured on either LN-511 or LN-421 expressed high level of basal markers (above 90% positive) and low expression of differentiation markers, comparable to control (3T3). This result was separately confirmed by immunostaining for these basal markers as well as transcription factor p63, which is known to regulate keratinocyte proliferation and is required for the development and maintenance of keratinocytes in human skin.

Example 5

The transcriptome of HEKs grown on LN-421, LN-511 and using 3T3 co-culture system was investigated by RNA-sequencing (RNA-seq). The results are seen in FIGS. 6A-6C.

Figures 6A, 6C:
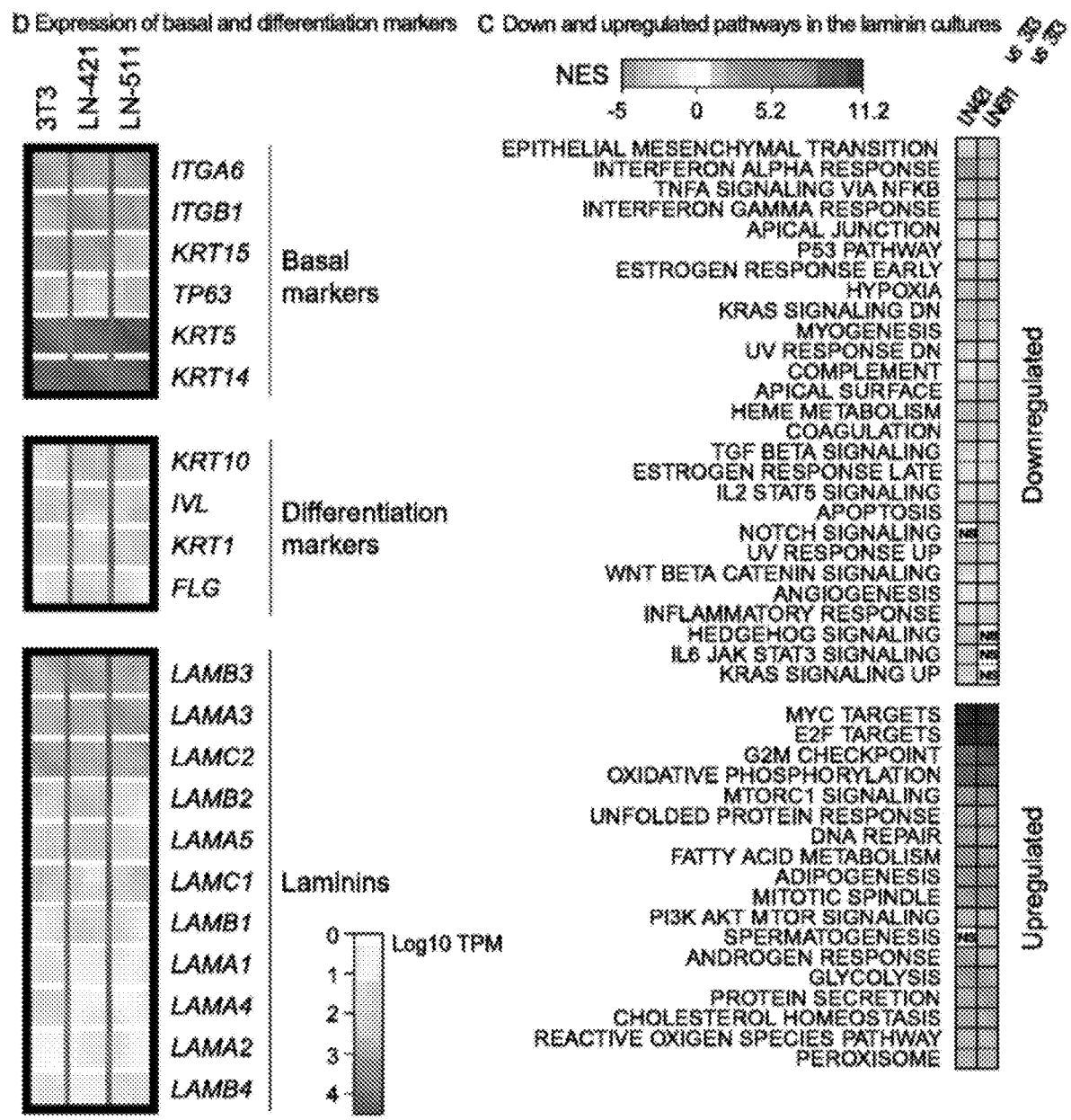
FIG. 6A is a heat map with expression levels of laminin genes and basal and differentiation keratinocyte marker genes (averaged across biological replicates and represented as log10 of transcripts per million, TPM).
FIG. 6C is a chart showing functional up and downregulated processes in keratinocytes growing on LN-421 and on LN-511, when compared against keratinocytes growing on 3T3 cells. Functional enrichment was computed by Gene Set Enrichment Analysis (GSEA). NES (normalized enrichment score) represents the strength of the enrichment. Non-significant processes are indicated with "NS". All other processes are significantly enriched (false discovery rate (FDR) <0.05).
Figure 6B:
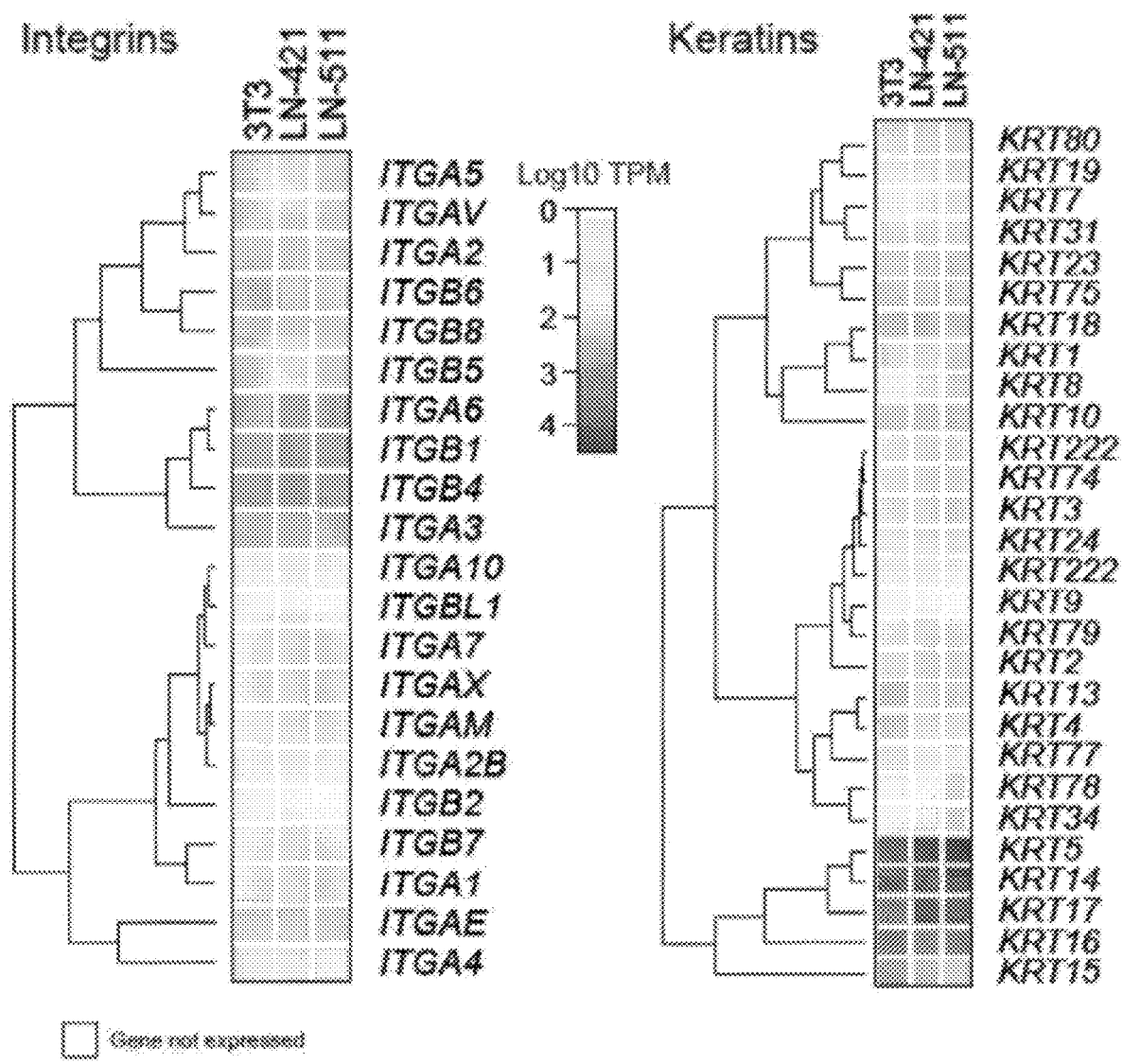
FIG. 6B is a heat map showing expression levels of integrin and keratin genes in keratinocytes growing on 3T3 co-culture, LN-421 and LN-511 (averaged across biological replicates and represented as log10 of transcripts per million, TPM). Only genes with a total sum of more than one TPM across all samples are shown. Genes were hierarchically clustered using the "complete" method.

As seen in FIG. 6A and FIG. 6B, basal and differentiation markers showed similar expression levels in the different three culture systems, confirming that the cells grown on the tested platforms were all progenitors. Overall, keratinocytes grown on LN-421 and LN-511 showed similar transcriptomic profiles (Spearman's ranked correlation of 0.99 and only 60 differentially expressed genes (false discovery rate, FDR<0.05).

More differences were found when comparing the transcriptome of the keratinocytes grown on the two laminins with the transcriptomic profile of cells grown using the 3T3 co-culture system (Spearman's ranked correlation of 0.94 and 0.95, 7,694 and 7,587 differentially expressed genes between keratinocytes grown on LN-511 and LN-421 when compared with the 3T3 co-culture respectively). This is seen in FIG. 6C. In keratinocytes grown on LN-421 or LN-511, significant downregulation (FDR<$10^{-6}$) was observed for genes involved in the "epithelial mesenchymal transition" and several pro-inflammatory pathways (e.g. "interferon alpha response", "interferon gamma response" and "TNFA signaling via NFKB"). Pro-inflammatory pathways are known to be upregulated in human skin keratinocytes when co-cultured with fibroblasts. Downregulation was also observed in genes involved in several developmental pathways (e.g. "TGF beta signaling" for LN-421 FDR=$9 \times 10^{-6}$ and LN-511 FDR=$1 \times 10^{-4}$, respectively, and "WNT beta catenin signaling" for LN-421 FDR=$4 \times 10^{-4}$ and LN-511 FDR=$1 \times 10^{-2}$, respectively). These keratinocytes also displayed a strong upregulation (FDR<$10^{-6}$) of "MYC targets" and cell cycle (i.e. "E2F targets" and "GM2 checkpoint") among other cellular processes. MYC has been shown to regulate keratinocyte adhesion and proliferation. Taken together, this data suggests that the transcriptome of the keratinocytes grown on LN-511 and LN-421 seemed to be less inflammatory and displayed more proliferative features than cells grown using the 3T3 co-culture system.

Example 6

Epidermis of glycerol-preserved allogeneic skin (EURO SKIN BANK, EA Beverwijk, The Netherlands) was removed mechanically after several cycles of snap-freezing and thawing. This de-epidermalised dermis (DED) was then cut into 2 cm×2 cm squares and the reticular side of the dermis was seeded with $5 \times 10^5$ human dermal fibroblasts with the help of a 1-cm diameter stainless steel ring. The next day, each DED was flipped and secondary keratinocytes culture that had been previously grown on either LN-421, LN-511, or co-cultured with 3T3 were seeded, $2 \times 10^5$ cells on each DED in cFAD culture medium. The cFAD culture medium was a mixture of DMEM and Ham's F12 at a ratio of 3:1, containing 10% fetal bovine serum, 5 pg/mL insulin, 0.18 mM adenine, 0.4 µg/mL hydrocortisone, 0.1 nM cholera toxin, 2 nM triiodothyronine, 10 ng/mL epidermal growth factor, and 50 IU/mL penicillin-streptomycin. Cultures were grown immersed in this medium for 7 days, then they were lifted to air-liquid interface for 14 days to stratify. Each sample was then processed for cryosection. Frozen sections were cut at 5 µm thickness and stained with H&E staining.

Figure 7A:
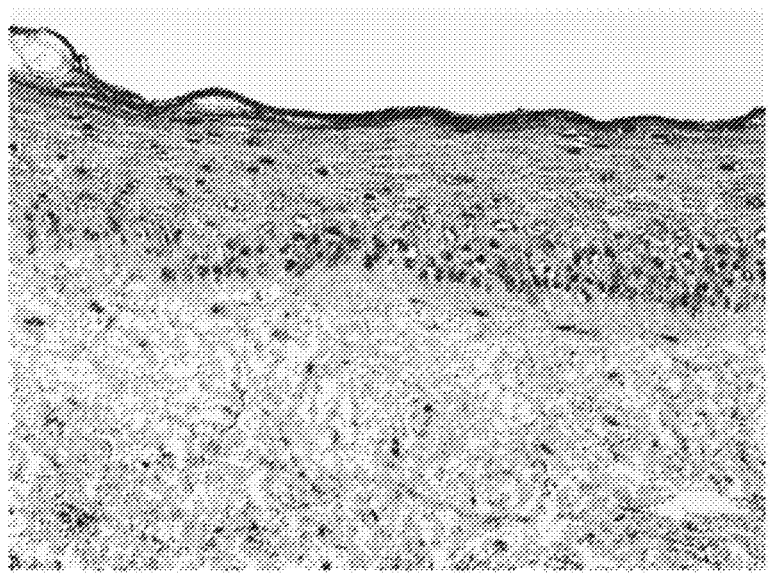
FIGS. 7A-7C are cross-sections of stainings of de-epidermalised dermis (DED) that has been seeded with keratinocytes previously grown on either LN-421, LN-511, or co-cultured with 3T3.
Figure 7B:
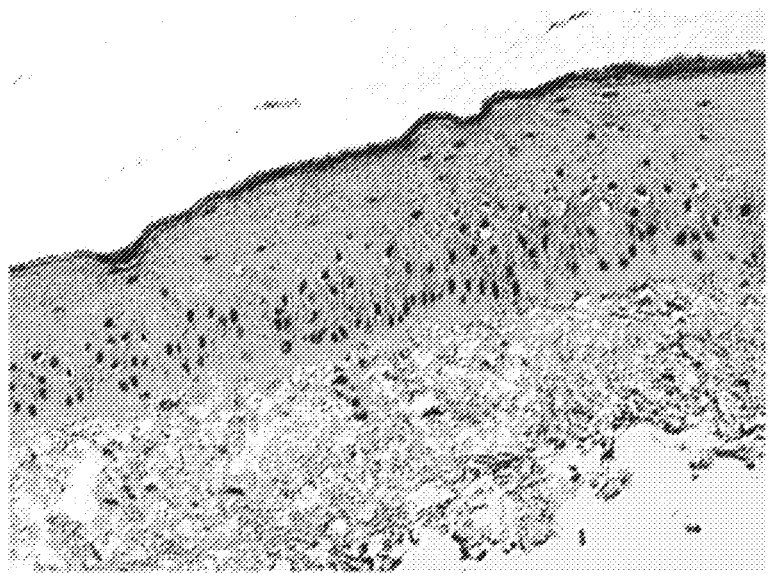
Figure 7C:
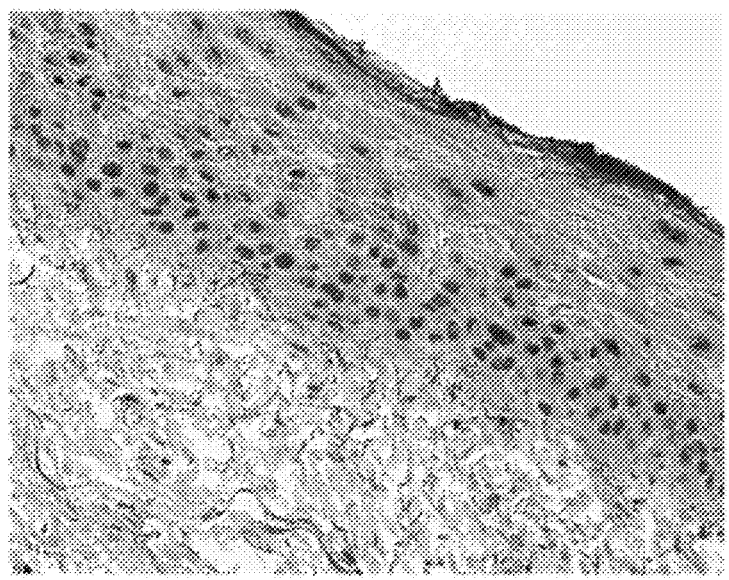

The resulting cross-sections are seen in FIGS. 7A-7C. This in-vitro functional assay showed that keratinocytes cultured on LN-511 and LN-421 were able to form thick, normal stratified epidermis comparable to the conventional Rheinwald & Green's method.

Example 7

To further validate these in vitro results, the functionality of these cells was further investigated in vivo by using a flap transplantation method as described by Barrandon et al., J. Investigative Dermatology, 91, 315-318 (1988). This method is suitable for assessing graft survival and for distinguishing between human epidermis generated by the graft from the epidermis of the recipient animal, as it minimizes graft contraction compared to conventional grafting. Fourteen days post-transplantation, human epidermis generated by keratinocytes cultured on either LN-511, LN-421, or using 3T3 co-cultures were harvested, sectioned and characterized by both Hematoxylin/Eosin (H&E) staining and immunostaining.

H&E staining revealed that the HEKs cultured either on LN-511 or LN-421 were able to generate a fully stratified epidermal layer in vivo. See FIGS. 8A-8C. To demonstrate that the formed epidermis was of human origin, and not from the host, the section was immunostained with anti-human Ku80 nuclear staining antibody. Next, immunofluorescence staining of basal and differentiation markers revealed that keratinocytes cultured on either LN-511 or LN-421 were stratified normally in vivo. Continuous laminin γ2 chain expression was observed underneath the basal layer of the generated human epidermis on both LN-511 and LN-421, suggesting that these transplanted HEKs secreted BM proteins (likely epithelial laminin, LN-332) and formed a functional epidermal layer.

SUMMARY

The present disclosure provides methods for culturing human epidermal keratinocytes in a xeno-free and fully defined system. Current methods for culturing and propagating human epidermal keratinocytes in serum-free medium require initial expansion in a feeder system for cell survival before they are collected and characterized. However, these methods cannot sustain keratinocyte growth in long-term culture (i.e., cells below fifth passage are typically used in characterization). The method described in the present disclosure enables more consistent and robust expansion of keratinocytes in a xeno-free and fully defined system without going through initial expansion by using a 3T3-feeder system.

With reference to FIGS. 1A-1J, keratinocytes cultured on a substrate with either LN-511 or LN-421 grew with greater efficiency than those keratinocytes cultured on a substrate with no laminin, LN-411, or LN-521.

With reference to FIG. 5, keratinocyte cells grown on LN-421 and LN-511 had high levels of basal markers and low expression of differentiation markers compared to the control, thereby implying that culturing keratinocytes on LN-421 or LN-511 in a chemically defined, xeno-free basal medium may be an alternative to growing keratinocytes in cultures containing animal cells while preserving their proliferative capacity. Therefore, this particular system reduces the risk of exposing any human cell culture to animal pathogens, allowing the cultured cell products to be used safely in the management of less severe burns and chronic wounds, since the system is xeno-free and fully defined.

Further, the epidermal keratinocytes grown using the disclosed methods above can be sustained for at least 10 passages, with differentiation markers starting to emerge after the seventh (7) passage, thereby improving over the typical five (5) passages current methods can support.

These methods allow for cultured therapeutic cell products, which are currently limited only to critical burn cases and severe vision loss due to safety concerns, to be used safely in the management of minor burns and chronic wounds. These cell products can also potentially be used for the treatment of any injuries or conditions in the human body (such as in the eye, bladder, oral cavity, intestine, etc.) with at least one epithelium defect. Further, there exists the possibility for wound coverage with cultured grafts without causing morbidity to the donor site, thereby improving quality of life for such patients.

The present disclosure has been described with reference to exemplary embodiments. Obviously, modifications and alterations will occur to others upon reading and understanding the preceding detailed description. It is intended that the present disclosure be construed as including all such modifications and alterations insofar that they come within the scope of the appended claims or the equivalents thereof.

The invention claimed is:

1. A method for expanding human keratinocytes, comprising:
    plating human keratinocytes on a substrate having a coating thereon, the coating consisting of laminin-511 and laminin-421; and
    culturing the keratinocytes in a xeno-free and chemically defined cell culture medium.

2. The method of claim 1, wherein the keratinocytes plated on the substrate are freshly isolated.

3. The method of claim 1, wherein the keratinocytes are plated on the substrate at a density of about $0.7 \times 10^5/cm^2$ to about $1.2 \times 10^5/cm^2$.

4. The method of claim 1, wherein the keratinocytes are cultured on the substrate at a temperature from about 30 degrees Celsius to about 40 degrees Celsius.

5. The method of claim 1, wherein the keratinocytes are cultured in an atmosphere containing from about 5% $CO_2$ to about 15% $CO_2$.

6. The method of claim 1, further comprising periodically dissociating and passaging the keratinocytes.

7. The method of claim 6, wherein the passaging of the keratinocytes occurs upon reaching a density of 1 cell to about $1.5 \times 10^4$ cells/$cm^2$.

8. The method of claim 1, wherein the weight ratio of laminin-511 to laminin-421 is from 15:1 to 1:15.

9. A method for treating a burn wound of a patient, comprising:
    plating keratinocyte cells taken from a donor site of the patient on a substrate having a coating that consists of laminin-511 and laminin-421;
    expanding the keratinocyte cells on the substrate in a xeno-free and chemically defined cell culture medium; and
    covering the burn wound with the keratinocyte cells from the substrate.

10. A method for treating a chronic wound of a patient, comprising:
    plating keratinocyte cells taken from a donor site of the patient on a substrate having a coating that consists of laminin-511 and laminin-421;
    expanding the keratinocyte cells on the substrate; and
    covering the wound with the keratinocyte cells from the substrate.

11. A method for treating any injuries or conditions in the human body, including cases in which only the epithelium is compromised, and/or in which an epithelium defect is a component of the injury, comprising:
    plating keratinocyte cells taken from a donor site of the patient on a substrate having a coating that consists of laminin-511 and laminin-421;
    expanding the keratinocyte cells on the substrate; and
    covering the epithelium defect with the keratinocyte cells from the substrate.

12. The method of claim 11, wherein the injuries or conditions in the human body are in an eye, the bladder, the oral cavity, or the intestine.

* * * * *